US012640230B2

(12) United States Patent
Didolkar et al.

(10) Patent No.: US 12,640,230 B2
(45) Date of Patent: May 26, 2026

(54) ACTIVE LEARNING FOR DISCOVERING PAIRWISE INTERACTIONS VIA REPRESENTATION LEARNING

(71) Applicant: Recursion Pharmaceuticals, Inc., Salt Lake City, UT (US)

(72) Inventors: Aniket Rajiv Didolkar, Montreal (CA); Jason Siyanda Hartford, Montreal (CA); Moksh Mukesh Kumar Jain, Montreal (CA)

(73) Assignee: Recursion Pharmaceuticals, Inc., Salt Lake City, UT (US)

( * ) Notice: Subject to any disclaimer, the term of this patent is extended or adjusted under 35 U.S.C. 154(b) by 13 days.

(21) Appl. No.: 18/639,146

(22) Filed: Apr. 18, 2024

(65) Prior Publication Data

US 2025/0259705 A1 Aug. 14, 2025

Related U.S. Application Data

(60) Provisional application No. 63/551,314, filed on Feb. 8, 2024.

(51) Int. Cl.
*G16B 25/10* (2019.01)
*G16B 40/00* (2019.01)

(52) U.S. Cl.
CPC ............. *G16B 25/10* (2019.02); *G16B 40/00* (2019.02)

(58) Field of Classification Search
None
See application file for complete search history.

(56) References Cited

U.S. PATENT DOCUMENTS 10,769,501 B1 9/2020 Ando et al.
12,073,638 B1 * 8/2024 Lazar et al.
(Continued)

FOREIGN PATENT DOCUMENTS

WO 2022-087540 A1 4/2022

OTHER PUBLICATIONS

Yu, Hengshi. "Deep Generative Models for Single-Cell Perturbation Experiments." ProQuest Dissertations & Theses, 2022. Print. (Year: 2022).*

(Continued)

*Primary Examiner* — Anna Skibinsky
*Assistant Examiner* — Joseph Pulliam
(74) *Attorney, Agent, or Firm* — Keller Preece PLLC

(57) ABSTRACT

The present disclosure relates to systems, non-transitory computer-readable media, and methods that a implement a framework for active learning to discover pairwise interactions via representation learning. Indeed, in one or more implementations, the disclosed systems generate a first individual perturbation embedding from a first representation of a first cell exposed to a first perturbation and a second individual perturbation embedding, from a second representation of a second cell exposed to a second perturbation. For instance, the disclosed systems combine the first individual perturbation embedding and the second individual perturbation embedding to determine a predicted pairwise embedding. Moreover, in some instances, the disclosed systems generate a pairwise embedding from a representation of a cell exposed to both the first and second perturbation. Additionally, from comparing the predicted pairwise embedding with the pairwise embedding, the disclosed systems generate a measure of biological interaction of the first and second perturbation.

20 Claims, 12 Drawing Sheets

(56) References Cited

U.S. PATENT DOCUMENTS

| | | | |
|---|---|---|---|
| 2019/0085324 | A1* | 3/2019 | Regev et al. |
| 2020/0362334 | A1* | 11/2020 | Regev et al. |
| 2021/0071256 | A1* | 3/2021 | Quigley et al. |
| 2023/0170040 | A1 | 6/2023 | Hauck |

OTHER PUBLICATIONS

Peidli, Stefan et al. "scPerturb: Harmonized Single-Cell Perturbation Data." Nature methods 21.3 (2024): 531-540. Web. (Year: 2024).*

Chandrasekaran, Srinivas Niranj et al. "Image-Based Profiling for Drug Discovery: Due for a Machine-Learning Upgrade?" Nature reviews. Drug discovery 20.2 (2021): 145-159. Web. (Year: 2021).*

Yu, Hengshi. PerturbNet Predicts Single-Cell Responses to Unseen Chemical and Genetic Perturbations. NewsRX LLC, 2022. Print. (Year: 2022).*

Bunne, Charlotte et al. "Learning Single-Cell Perturbation Responses Using Neural Optimal Transport." Nature methods 20.11 (2023): 1759-1768. Web. (Year: 2023).*

Alessandro Palma, Fabian J. Theis, Mohammad Lotfollahi bioRxiv 2023.07.17.549216; doi: https://doi.org/10.1101/2023.07.17.549216 (Year: 2023).*

Sun H, Murphy RF. Evaluation of categorical matrix completion algorithms: toward improved active learning for drug discovery. Bioinformatics. Oct. 25, 2021;37(20):3538-3545 (Year: 2021).*

Osorio, Daniel et al. "scTenifoldKnk: An Efficient Virtual Knockout Tool for Gene Function Predictions via Single-Cell Gene Regulatory Network Perturbation." Patterns (New York, N.Y.) 3.3 (2022): 100434-100434. Web. (Year: 2022).*

Caldera, Michael et al. "Mapping the Perturbome Network of Cellular Perturbations." Nature communications 10.1 (2019): 5140-14. Web. (Year: 2019).*

Roohani, Yusuf, Kexin Huang, and Jure Leskovec. "Predicting Transcriptional Outcomes of Novel Multigene Perturbations with GEARS." Nature biotechnology 42.6 (2023): 927-935. Web. (Year: 2023).*

Feldman, David et al. "Pooled Genetic Perturbation Screens with Image-Based Phenotypes." Nature protocols 17.2 (2022): 476-512. Web. (Year: 2022).*

Cheng, Junyun et al. "Massively Parallel CRISPR-Based Genetic Perturbation Screening at Single-Cell Resolution." Advanced science 10.4 (2023): e2204484-n/a. Web. (Year: 2023).*

A. Foster. Variational, Monte Carlo and Policy-Based Approaches to Bayesian Experimental Design, PhD thesis, University of Oxford, 2021.

A. Karbasi, V. Mirrokni, and M. Shadravan. Parallelizing Thompson Sampling. Advances in Neural Information Processing Systems, 34:10535-10548, 2021.

A. Mehrjou, A. Soleymani, A. Jesson, P. Notin, Y. Gal, S. Bauer, and P. Schwab. GeneDisco: A Benchmark for Experimental Design in Drug Discovery. In International Conference on Learning Representations, arXiv:2110.11875v1, Oct. 22, 2021.

A. Pacchiano, D. Wulsin, R. A. Barton, and L. Voloch. Neural Design for Genetic Perturbation Experiments. In The Eleventh International Conference on Learning Representations, 2023b.

A. Pacchiano, J. Lee, and E. Brunskill. Experiment Planning with Function Approximation. In Thirty-seventh Conference on Neural Information Processing Systems, 2023a.

A. Zanette, K. Dong, J. N. Lee, and E. Brunskill. Design of Experiments for Stochastic Contextual Linear Bandits. Advances in Neural Information Processing Systems, 34:22720-22731, 2021.

C. Lyle, A. Mehrjou, P. Notin, A. Jesson, S. Bauer, Y. Gal, and p. Schwab. DiscoBAX: Discovery of Optimal Intervention Sets in Genomic Experiment Design. In International Conference on Machine Learning, pp. 23170-23189. PMLR, 2023.

D. Kuzuoglu-Ozturk, Z. Hu, M. Rama, E. Devericks, J. Weiss, G. G. Chiang, S. T. Worland, S. E. Brenner, H. Goodarzi, L. A. Gilbert, et al. Revealing molecular pathways for cancer cell fitness through a genetic screen of the cancer translatome. Cell Reports, 35(13), 2021.

D. Phan, N. Pradhan, and M. Jankowiak. Composable Effects for Flexible and Accelerated Probabilistic Programming in NumPyro. arXiv preprint arXiv:1912.11554v1, Dec. 24, 2019.

D. Russo and B. Van Roy. An Information-Theoretic Analysis of Thompson Sampling. The Journal of Machine Learning Research, 17(1):2442-2471, 2016.

D. Szklarczyk, A. L. Gable, K. C. Nastou, D. Lyon, R. Kirsch, S. Pyysalo, N. T. Doncheva, M. Legeay, T. Fang, P. Bork, et al. The string database in 2021: customizable protein-protein networks, and functional characterization of user-uploaded gene/measurement sets. Nucleic acids research, 49 (D1):D605-D612, 2021.

D. V. Lindley. On a Measure of the Information Provided by an Experiment. The Annals of Mathematical Statistics, 27(4):986-1005, 1956.

D. Wingate and T. Weber. Automated Variational Inference in Probabilistic Programming. arXiv preprint arXiv:1301.1299v1, Jan. 7, 2013.

D. Xun, R.Wang, X. Zhang, and Y.Wang. Microsnoop: A Generalized Tool for Unbiased Representation of Diverse Microscopy Images. bioRxiv, 2023. doi: 10.1101/2023.02.25.530004. URL https://www.biorxiv.org/content/early/2023/05/06/2023.02.25.530004.

E. Bingham, J. P. Chen, M. Jankowiak, F. Obermeyer, N. Pradhan, T. Karaletsos, R. Singh, P. A. Szerlip, P. Horsfall, and N. D. Goodman. Pyro: Deep Universal Probabilistic Programming. J. Mach. Learn. Res., 20:28:1-28:6, 2019. URL http://jmlr.org/papers/v20/18-403.html.

E. G. Ryan, C. C. Drovandi, J. M. McGree, and A. N. Pettitt. A Review of Modern Computational Algorithms for Bayesian Optimal Design. International Statistical Review, 84(1):128-154, 2016.

G. Huang, Z. Liu, L. Van Der Maaten, and K. Q. Weinberger. Densely Connected Convolutional Networks. In Proceedings of the IEEE conference on computer vision and pattern recognition, pp. 4700-4708, 2017.

G. Roeder, L. Metz, and D. Kingma. On Linear Identifiability of Learned Representations. In M. Meila and T. Zhang, editors, Proceedings of the 38th International Conference on Machine Learning, vol. 139 of Proceedings of Machine Learning Research, pp. 9030-9039. PMLR, Jul. 18-24, 2021. URL https://proceedings.mlr.press/v139/roeder21a.html.

H. Robbins. Some Aspects of the Sequential Design of Experiments. 1952.

J. A. Doudna and E. Charpentier. The new frontier of genome engineering with CRISPR-Cas9. Science, 346(6213):1258096, 2014.

K. Drew, J. B. Wallingford, and E. M. Marcotte. hu. MAP 2.0: integration of over 15,000 proteomic experiments builds a global compendium of human multiprotein assemblies. Molecular systems biology, 17(5):e10016, 2021.

K. Huang, R. Lopez, J.-C. Hutter, T. Kudo, A. Rios, and A. Regev. Sequential Optimal Experimental Design of Perturbation Screens Guided by Multi-modal Priors. bioRxiv, pp. 2023-12, 2023.

L. Licata, P. Lo Surdo, M. Iannuccelli, A. Palma, E. Micarelli, L. Perfetto, D. Peluso, A. Calderone, L. Castagnoli, and G. Cesareni. SIGNOR 2.0, the SIGnaling Network Open Resource 2.0: 2019 update. Nucleic Acids Research, 48(D1):D504-D510, 2020.

M. Bereket and T. Karaletsos. Modelling Cellular Perturbations with the Sparse Additive Mechanism Shift Variational Autoencoder. In Thirty-seventh Conference on Neural Information Processing Systems, 2023. URL https://openreview.net/forum?id=DzaCE00jGV.

M. Giurgiu, J. Reinhard, B. Brauner, I. Dunger-Kaltenbach, G. Fobo, G. Frishman, C. Montrone, and A. Ruepp. CORUM: the comprehensive resource of mammalian protein complexes—2019. Nucleic Acids Research, 47(D1):D559-D563, 2019.

M. Jinek, K. Chylinski, I. Fonfara, M. Hauer, J. A. Doudna, and E. Charpentier. A programmable dual RNA-guided DNA endonuclease in adaptive bacterial immunity. Science, 337(6096):816-821, 2012.

M. Lotfollahi, A. Klimovskaia Susmelj, C. De Donno, L. Hetzel, Y. Ji, I. L. Ibarra, S. R. Srivatsan, M. Naghipourfar, R. M. Daza, B. Martin, J. Shendure, J. L. McFaline-Figueroa, P. Boyeau, F. A. Wolf, N. Yakubova, S. Gunnemann, C. Trapnell, D. Lopez-Paz, and F. J. Theis. Predicting cellular responses to complex perturbations in

(56) References Cited

OTHER PUBLICATIONS high-throughput screens. Molecular Systems Biology, 19(6):e11517, 2023. doi: https://doi.org/10.15252/msb.202211517. URL https://www.embopress.org/doi/abs/10.15252/msb.202211517.

M. M. Fay, O. Kraus, M. Victors, L. Arumugam, K. Vuggumudi, J. Urbanik, K. Hansen, S. Celik, N. Cernek, G. Jagannathan, et al. RxRx3: Phenomics Map of Biology. bioRxiv, pp. 2023-02, 2023.

M. Sypetkowski, M. Rezanejad, S. Saberian, O. Kraus, J. Urbanik, J. Taylor, B. Mabey, M. Victors, J. Yosinski, A. R. Sereshkeh, et al. RxRx1: A Dataset for Evaluating Experimental Batch Correction Methods. In Proceedings of the IEEE/CVF Conference on Computer Vision and Pattern Recognition, pp. 4284-4293, arXiv2301. 05768v1, Jan. 13, 2023.

N. Moshkov, M. Bornholdt, S. Benoit, M. Smith, C. McQuin, A. Goodman, R. A. Senft, Y. Han, M. Babadi, P. Horvath, et al. Learning representations for image-based profiling of perturbations. Biorxiv, pp. 2022-08, 2022.

N. Srinivas, A. Krause, S. Kakade, and M. Seeger. Gaussian Process Optimization in the Bandit Setting: No. Regret and Experimental Design. In Proceedings of the 27th International Conference on International Conference on Machine Learning, pp. 1015-1022, 2010.

O. Kraus, K. Kenyon-Dean, S. Saberian, M. Fallah, P. McLean, J. Leung, V. Sharma, A. Khan, J. Balakrishnan, S. Celik, et al. Masked Autoencoders are Scalable Learners of Cellular Corphology. arXiv preprint arXiv:2309.16064v2, Nov. 27, 2023.

P. Sebastiani and H. P. Wynn. Maximum entropy sampling and optimal Bayesian experimental design. Journal of the Royal Statistical Society: Series B (Statistical Methodology), 62(1):145-157, 2000.

R. Combes, M. S. Talebi Mazraeh Shahi, A. Proutiere, et al. Combinatorial Bandits Revisited. Advances in neural information processing systems, 28, 2015.

R. Garnett, Y. Krishnamurthy, X. Xiong, J. Schneider, and R. Mann. Bayesian Optimal Active Search and Surveying. In Proceedings of the 29th International Conference on International Conference on Machine Learning, pp. 843-850, 2012.

R. Lopez, N. Tagasovska, S. Ra, K. Cho, J. Pritchard, and A. Regev. Learning Causal Representations of Single Cells via Sparse Mechanism Shift Modeling. In M. van der Schaar, C. Zhang, and D. Janzing, editors, Proceedings of the Second Conference on Causal Learning and Reasoning, vol. 213 of Proceedings of Machine Learning Research, pp. 662-691. PMLR, Apr. 11-14, 2023. URL https://proceedings.mlr.press/v213/lopez23a.html.

R. Ranganath, S. Gerrish, and D. Blei. Black Box Variational Inference. In Artificial intelligence and statistics, pp. 814-822. PMLR, 2014.

S. M. Nijman. Synthetic lethality: General principles, utility and detection using genetic screens in human cells. FEBS Letters, 585(1):1-6, 2011. ISSN 0014-5793.

S. N. Chandrasekaran, J. Ackerman, E. Alix, D. M. Ando, J. Arevalo, M. Bennion, N. Boisseau, A. Borowa, J. D. Boyd, L. Brino, P. J. Byrne, et al. JUMP Cell Painting dataset: morphological impact of 136,000 chemical and genetic perturbations. bioRxiv, 2023.

T. Desautels, A. Krause, and J. W. Burdick. Parallelizing Exploration-Exploitation Tradeoffs in Gaussian Process Bandit Optimization. Journal of Machine Learning Research, 15:3873-3923, 2014.

T. Lattimore and C. Szepesvári. Bandit Algorithms. Cambridge University Press, 2020.

T. Rainforth, A. Foster, D. R. Ivanova, and F. B. Smith. Modern Bayesian Experimental Design. arXiv preprint arXiv:2302. 14545v2, Nov. 29, 2023.

T. Rainforth, R. Cornish, H. Yang, A. Warrington, and F. Wood. On Nesting Monte Carlo Estimators. In International Conference on Machine Learning, pp. 4267-4276. PMLR, 2018.

V. Kanade, H. B. McMahan, and B. Bryan. Sleeping Experts and Bandits with Stochastic Action Availability and Adversarial Rewards. In Artificial Intelligence and Statistics, pp. 272-279. PMLR, 2009.

W. Chen, Y. Wang, and Y. Yuan. Combinatorial Multi-Armed Bandit: General Famework, Results and Applications. In International conference on machine learning, pp. 151-159. PMLR, 2013.

W. R. Thompson. On the Likelihood that One Unknown Probability Exceeds Another in View of the Evidence of Two Samples. Biometrika, 25(3-4):285-294, 1933.

Z. Dai, Q. P. Nguyen, S. S. Tay, D. Urano, R. Leong, B. K. H. Low, and P. Jaillet. Batch Bayesian Optimization for Replicable Experimental Design. arXiv preprint arXiv:2311.01195v1, Nov. 2, 2023.

Z. Wang, L. Gui, J. Negrea, and V. Veitch. Concept Algebra for (Score-Based) Text-Controlled Generative Models. In Thirty-seventh Conference on Neural Information Processing Systems, 2023. URL https://openreview.net/forum?id=SGIrCuwdsB.

Z. Xu, E. Shim, A. Tewari, and P. Zimmerman. Adaptive Sampling for Discovery. Advances in Neural Information Processing Systems, 35:1114-1126, 2022.

GitHub - Google/JAX Composable transformation of Phython+ NumPy programs. 6 pages [retrieved on Jun. 7, 2024]. Retrieved from the Internet: https://github.com/jax-ml/jax.

Mark-Anthony Bray et al. Cell Painting, a high-content image-based assay for morphological profiling using multiplexed fluorescent dyes. Nature Protocols, 11(9):1757-1774, 2016.

International Search Report and Written Opinion as received in PCT/US2025/011845 dated Apr. 21, 2025.

* cited by examiner

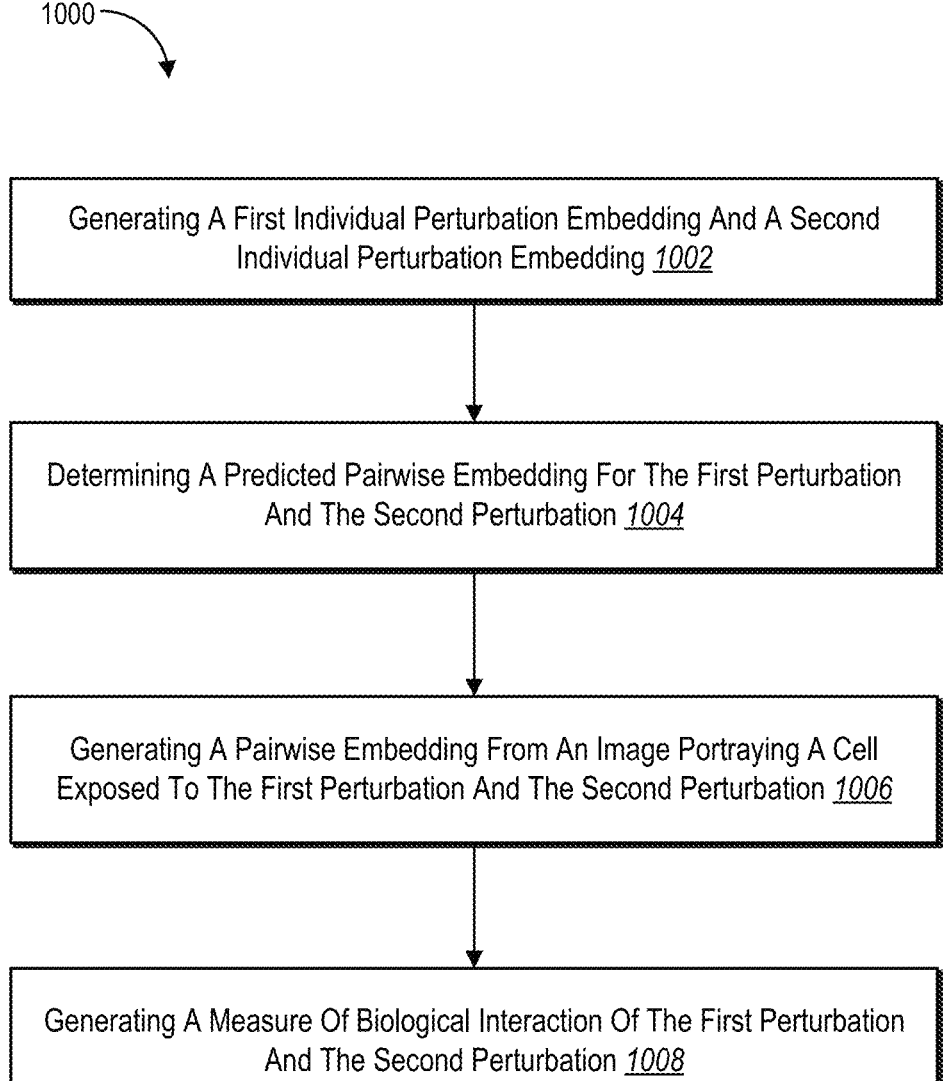

1000

Generating A First Individual Perturbation Embedding And A Second Individual Perturbation Embedding 1002

Determining A Predicted Pairwise Embedding For The First Perturbation And The Second Perturbation 1004

Generating A Pairwise Embedding From An Image Portraying A Cell Exposed To The First Perturbation And The Second Perturbation 1006

Generating A Measure Of Biological Interaction Of The First Perturbation And The Second Perturbation 1008

Fig. 10

ACTIVE LEARNING FOR DISCOVERING PAIRWISE INTERACTIONS VIA REPRESENTATION LEARNING

CROSS REFERENCE TO RELATED APPLICATIONS

This application claims the benefit of and priority to U.S. Provisional Application No. 63/551,314, filed Feb. 8, 2024. The aforementioned application is hereby incorporated by reference in its entirety.

BACKGROUND

Recent years have seen significant developments in hardware and software platforms for predicting perturbation impact on underlying cell behavior. For example, conventional systems capture microscopy images of cells that have been stained with various dyes to expose different cellular components and reveal the effect of various perturbations on the cell. Despite these recent advances, conventional systems suffer from a number of technical deficiencies, particularly with regard to accuracy, efficiency, and operational inflexibility.

SUMMARY

Embodiments of the present disclosure provide benefits and/or solve one or more of the foregoing or other problems in the art with systems, non-transitory computer-readable media, and methods for actively learning pairwise interactions between perturbations via representation learning. In particular, in one or more implementations the disclosed systems compare machine learning representations of individual perturbations and perturbation pairs to identify new pairwise biological interactions. Moreover, the disclosed systems can utilize active learning approaches to identify new pairwise perturbations to explore in identifying additional, previously undetected interactions. Specifically, in one or more implementations the disclosed systems generate individual perturbation embeddings (e.g., a first individual perturbation embedding and a second individual perturbation embedding) from individual phenomic representations and determine a predicted pairwise embedding from combining the individual perturbation embeddings. Further, in some embodiments, the disclosed systems generate a pairwise embedding from a pairwise experiment (e.g., a double perturbation for a single cell) and compare the pairwise embedding with the predicted pairwise embedding to generate a measure of biological interaction. Indeed, in one or more implementations, the disclosed systems can detect the measure of biological interaction by identifying a difference between the predicted pairwise embedding (from individual perturbation embeddings) relative the pairwise embedding of an actual pairwise experiment.

Moreover, in some embodiments, the disclosed systems efficiently search a space of perturbation pairs to identify new perturbation pairs for further exploration. Specifically, in one or more implementations, the disclosed systems utilize one or more active learning approaches to select an additional perturbation pair for further pairwise experimentation. To illustrate, in one or more implementations, the disclosed systems generate a matrix and utilize an active-matrix completion algorithm to identify perturbation pairs that are most likely to have meaningful interactions (e.g., a biological activity beyond that expected from the individual perturbations themselves). Additionally, from the identified perturbation pair, the disclosed systems initiate performance of a downstream experiment for a cell to be exposed to the perturbation pair. In this manner, the disclosed systems can efficiently and accurately utilize machine learning embeddings to explore and identify previously unknown biological interactions between perturbations.

Additional features and advantages of one or more embodiments of the present disclosure are outlined in the description which follows, and in part will be obvious from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

FIG. 10 illustrates an example series of acts to generate a measure of biological interaction in accordance with one or more embodiments.

DETAILED DESCRIPTION

Embodiments of the present disclosure provide benefits and/or solve one or more of the foregoing or other problems in the art with systems, non-transitory computer-readable media, and methods of a framework for active learning to discover pairwise interactions via representation learning. For example, the multi-perturbation interaction system uses phenomic embeddings (e.g., individual perturbation and pairwise embeddings) and active learning to efficiently identify pairwise perturbations (e.g., gene knockouts) that have an added biological interaction (e.g., a biological activity beyond that expected from the individual knockouts themselves). To illustrate, the multi-perturbation interaction system utilizes machine learning models to generate embeddings from single perturbation representations (e.g., phenomic images resulting from a single gene knockout). In some embodiments, the multi-perturbation interaction system then combines embeddings for the individual perturbations to generate a predicted pairwise embedding for a pairwise perturbation. Moreover, in some embodiments, the multi-perturbation interaction system compares the predicted pairwise embedding with an actual pairwise embedding (e.g., resulting from multiple perturbations) to generate a measure of biological interaction (e.g., an interaction score).

In some embodiments, the measure of biological interaction reflects a comparison, or difference, between individual perturbation embeddings and an actual pairwise embedding. For instance, the interaction score reflects added biological interactions resulting from the perturbation combination within a cell. In this manner, the multi-perturbation interaction system can detect a biological interaction from the high dimensional output of a pairwise experiment. In addition, the multi-perturbation interaction system can also utilize active learning to avoid running all perturbation pairs (e.g., all pairs of gene knockouts) to recover pairwise biological relationships. For instance, the multi-perturbation interaction system can generate a matrix of different perturbations and corresponding measures of biological interactions (e.g., for already known pairwise perturbations). Further, the multi-perturbation interaction system can efficiently explore the interaction space using active learning approaches. For example, by treating the measures of biological interactions as a reward, the multi-perturbation interaction system can reduce the problem of finding additional perturbation pairs to an active-matrix completion problem. In some implementations, the multi-perturbation interaction system balances exploration and exploitation to select different entries (e.g., perturbation pairs) for initiating downstream experimentation.

Figure 1A:
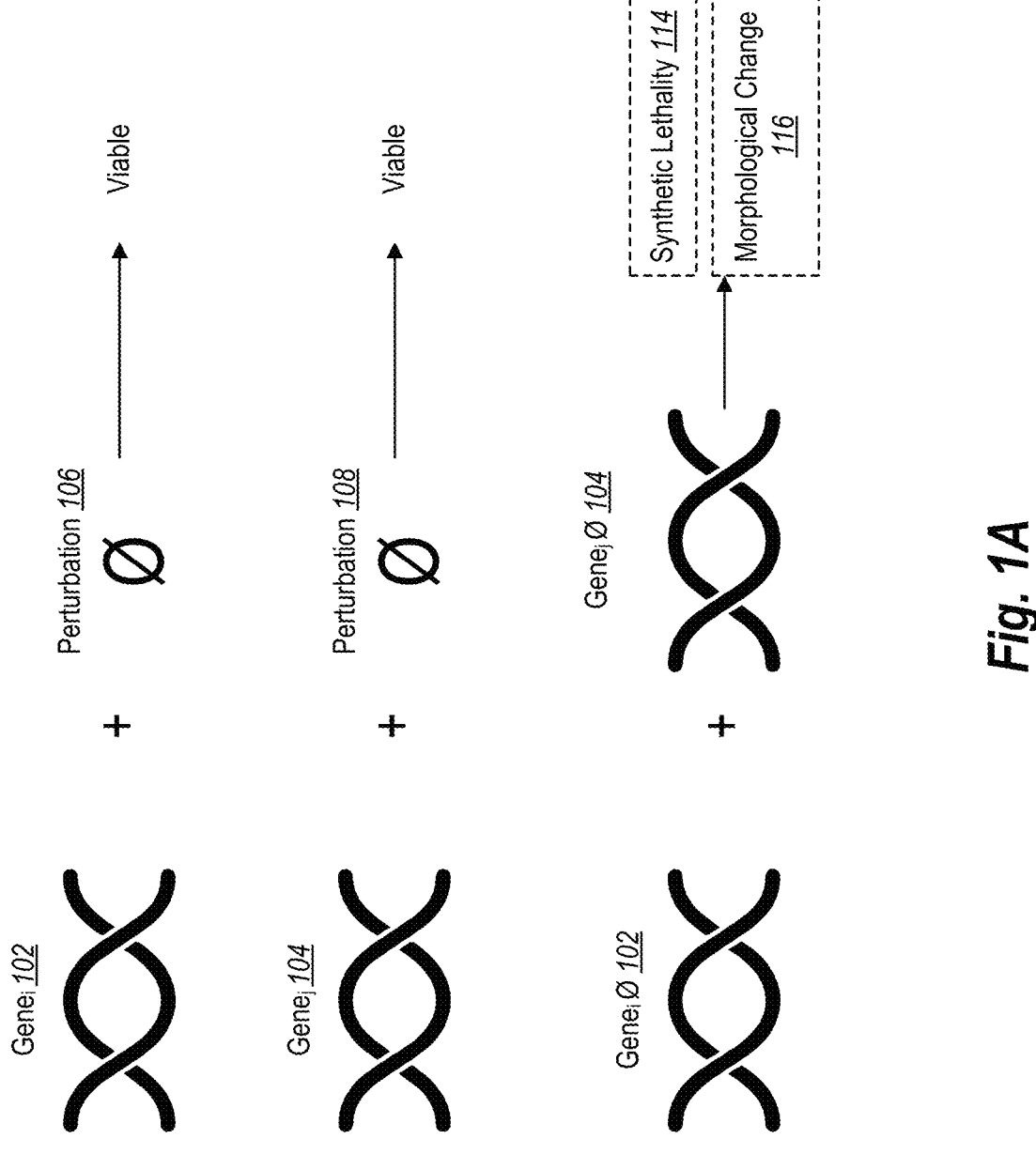
FIG. 1A illustrates an overview diagram of pairwise perturbations revealing biological interactions not indicated by single perturbation representations in accordance with one or more embodiments.

As shown, FIG. 1A illustrates different biological results for different perturbations. For example, embeddings of microscopy images from single perturbations can be used to infer biological interactions but are limited to interactions that are revealed by single perturbations. Specifically, single perturbation experiments (e.g., single gene knockouts) involve thousands of experiments (e.g., 17,000 experiments for single gene knockouts), however pairwise perturbations involve exponentially more (e.g., 200 million for double gene knockouts).

FIG. 1A illustrates a gene 102 (gene$_i$) exposed to a first perturbation 106, and despite the first perturbation 106, a first cell that includes the gene 102 is still viable. Further, FIG. 1A shows a gene 104 (gene$_j$) exposed to a second perturbation 108, and despite the second perturbation 108, a second cell that includes the gene 104 is still viable. In contrast, a third cell exposed to both the first perturbation 106 and the second perturbation 108 (e.g., which results in knocking out the gene 102 and the gene 104) results in synthetic lethality 114 (e.g., apoptosis) and/or a morphological change 116. In other words, FIG. 1A shows that single perturbation experiments often do not reveal valuable biological interactions observable from pairwise perturbations.

Figure 1B:
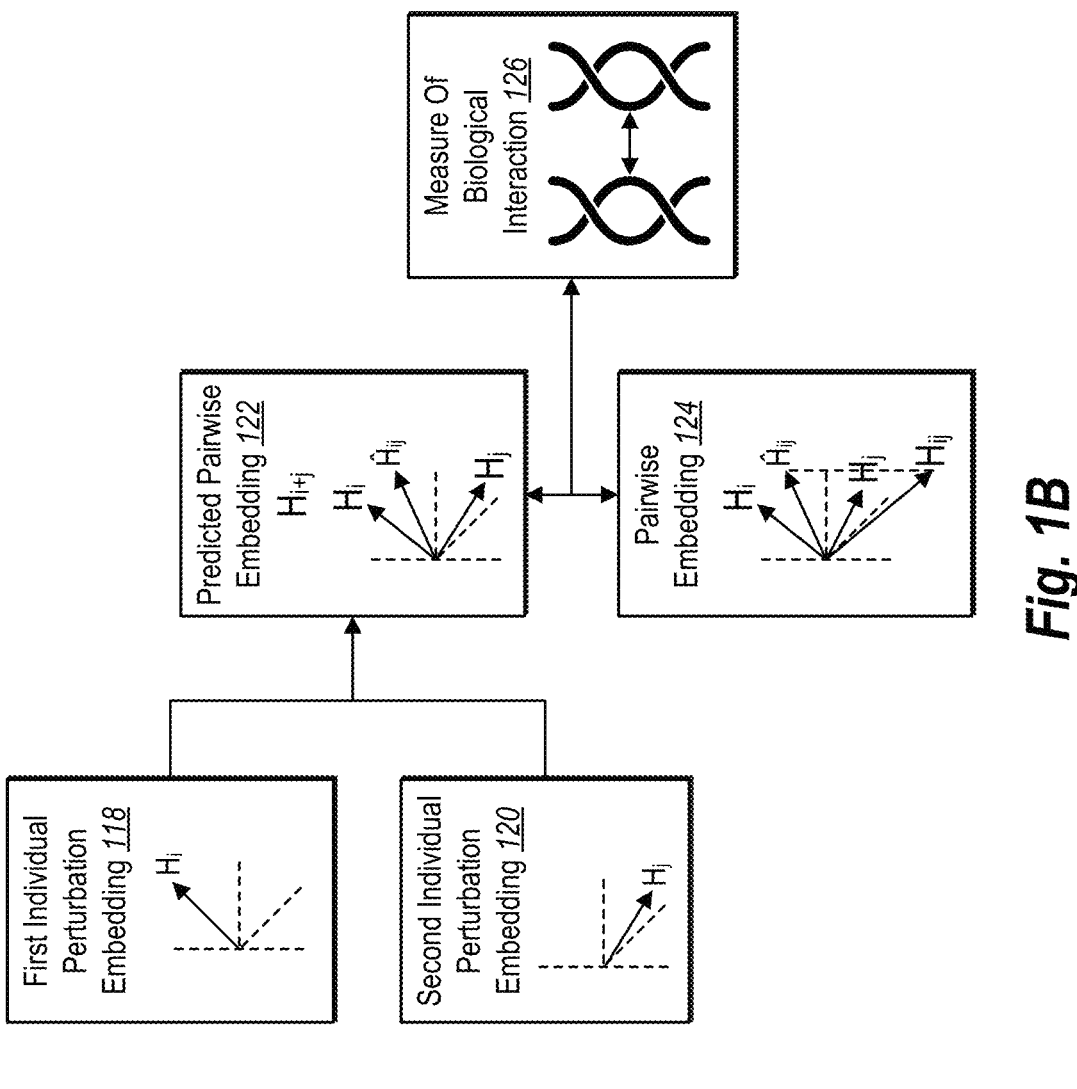
FIG. 1B illustrates a multi-perturbation interaction system generating a measure of biological interaction utilizing pairwise embeddings and individual perturbation embeddings in accordance with one or more embodiments.

FIG. 1B illustrates an overview diagram of the multi-perturbation interaction system detecting biological interactions from high dimensional outputs of a pairwise experiment in accordance with one or more embodiments. As shown in FIG. 1B, a multi-perturbation interaction system 100 receives individual perturbation embeddings for cells exposed to individual perturbations. Specifically, FIG. 1B shows the multi-perturbation interaction system 100 receiving a first individual perturbation embedding 118 and a second individual perturbation embedding 120.

As used herein, the term "perturbation" (e.g., cell perturbation) refers to an alteration or disruption to a cell or the cell's environment (to elicit potential phenotypic changes to the cell). In particular, the term perturbation can include a gene perturbation (i.e., a gene-knockout perturbation) or a compound perturbation (e.g., a molecule perturbation or a soluble factor perturbation). These perturbations are accomplished by performing a perturbation experiment. A perturbation experiment refers to a process for a perturbation to a cell. A perturbation experiment also includes a process for developing/growing the perturbed cell into a resulting phenotype.

As used herein, the term "individual perturbation" refers to the multi-perturbation interaction system 100 exposing a cell to a single perturbation. Specifically, the multi-perturbation interaction system 100 performs a perturbation experiment that involves an individual perturbation to the cell. For example, the multi-perturbation interaction system 100 performs a single gene knockout on the cell.

As used herein, the term "individual perturbation embedding" (or perturbation embeddings, individual perturbation image embeddings or phenomic image embeddings) refers to a numerical representation of a cell representation resulting from an individual perturbation to a cell. For example, an individual perturbation embedding includes a vector representation of a perturbation image generated by a machine learning model (e.g., a convolutional neural network, masked autoencoder, or other machine learning embedding model). Thus, an individual perturbation embedding includes a feature vector generated by application of various convolutional neural network layers (at different resolutions/dimensionality).

As shown, the multi-perturbation interaction system 100 combines the first individual perturbation embedding 118 and the second individual perturbation embedding 120 to generate a predicted pairwise embedding 122. As used herein, the term "predicted pairwise embedding" refers to a numerical representation of combining a pair of individual perturbation embeddings. Specifically, the predicted pairwise embedding 122 refers to an embedding prediction for perturbing a cell with a first and second perturbation without actually perturbing the cell with both perturbations. For example, the multi-perturbation interaction system 100 determines the predicted pairwise embedding 122 by normalizing and combining (e.g., adding, averaging, or blending) the individual perturbation embeddings.

Further, as shown in FIG. 1B, the multi-perturbation interaction system 100 receives a pairwise embedding 124. As used herein, the term "pairwise embedding" refers to a numerical representation of a cell representation resulting from a cell exposed to a first perturbation and a second perturbation (or additional perturbations). Specifically, the pairwise embedding 124 can refer to generating an embedding (using a machine learning model) from an image of a cell exposed to a double perturbation (e.g., a double gene knockout). In contrast with the individual perturbations, the pairwise embedding 124 comes from a cell image with a double perturbation. Although many embodiments described in this application refer to two perturbations, the multi-perturbation interaction system 100 can also perform similar functions with embeddings reflecting three or more perturbations (e.g., multi-perturbation embedding).

Moreover, as shown, the multi-perturbation interaction system 100 compares the predicted pairwise embedding 122 with the pairwise embedding 124 to generate a measure of biological interaction 126. As used herein, the term "a measure of biological interaction" refers to a value that indicates a relationship between perturbations. In particular, a measure of biological interaction includes a measure or indication of interaction between two perturbations (e.g., in addition to biological impacts of the individual perturbations). In other words, the measure of biological interaction can indicate biological activity beyond that expected from the individual perturbations themselves, such as synthetic lethality-style interactions (e.g., apoptosis) or morphological cell changes that result from double perturbations. Specifically, the measure of biological interaction helps the multi-perturbation interaction system 100 identify when a double perturbation to a cell has an effect that single perturbations to a cell on their own would not uncover. For instance, in some embodiments, double gene knockouts result in specific changes to a cell that would not manifest (or would manifest to a different degree) from individual gene knockouts.

Although FIGS. 1A-1B discuss double perturbations or pairwise experimentation, in one or more embodiments, the multi-perturbation interaction system 100 deals with multi-perturbations for a single cell and multi-pair experimentation. Specifically, the multi-perturbation interaction system 100 receives a triplet embedding (e.g., resulting from a triple perturbation to a single cell) and compares the triplet embedding with a predicted triplet embedding generated by combining individual perturbation embeddings to generate a measures of biological interaction.

As mentioned briefly above, conventional systems suffer from a number of technical deficiencies with regard to implementing computing devices. For example, conventional systems often suffer from computational inaccuracies. Specifically, conventional systems often rely on single perturbation experiments to infer potential relationships. However, due to the reliance on single perturbation experiments to infer pairwise relationships, conventional systems struggle with identifying biological relationships that only manifest from double perturbation experiments.

Some conventional systems attempt to remedy the issue of uncovering biological relationships only apparent through double perturbation experiments by performing double perturbation experiments. As an initial matter, performing double perturbation experiments themselves utilizing conventional approaches often fails to accurately reflect or uncover the biological interaction between the perturbations. Indeed, biological interactions between perturbations can be subtle changes that impact the gradient or cumulative impact of individual perturbations. Unless a cell actually dies, conventional systems are often unable to identify such subtle compounding biological impacts resulting from multiple perturbations.

In addition, however, conventional systems that perform double perturbation experiments are extremely inefficient with regard to time, computational costs, and memory expenditures for implementing computing devices in the genetic space. For instance, running double knockout gene experiments requires running upwards of 200 million experiments. As such, conventional systems face hurdles of not having access to enough time, robotics equipment, memory, or processing power to sufficient experiments to analyze perturbation combinations.

Relatedly, conventional systems further suffer from operational inflexibility due to conventional systems being limited in identifying only certain biological interactions. As mentioned, conventional systems are typically confined to data involving single perturbations and as such, fail to identify more complex interactions.

In one or more embodiments, the multi-perturbation interaction system 100 overcomes the deficiencies of conventional systems. For example, in some embodiments, the multi-perturbation interaction system 100 overcomes inaccuracies of conventional systems by utilizing both individual perturbation embeddings and a pairwise embedding (for a pairwise perturbation experiment already performed). In particular, the multi-perturbation interaction system 100 compares a combination of the individual perturbation embeddings with the pairwise embedding to generate a measure of biological interaction. In contrast to conventional systems that rely on single perturbation experiments, the multi-perturbation interaction system 100 infers pairwise relationships from the comparison (e.g., of individual embeddings with the pairwise embedding) to uncover subtle biological relationships that become apparent from the pairwise perturbation. As such, the multi-perturbation interaction system 100 more accurately identifies changes to a cell resulting from pairwise perturbations.

In one or more embodiments, the multi-perturbation interaction system 100 further overcomes inefficiencies of conventional systems. For instance, the multi-perturbation interaction system 100 utilizes active learning to efficiently identify additional perturbation pairs that are likely to exhibit significant biological interactions. To illustrate, the multi-perturbation interaction system 100 generates a measure of biological interaction for a pairwise perturbation utilizes active-matrix completion (or another prediction approach) to further identify meaningful biological relationships. For instance, the multi-perturbation interaction system 100 identifies additional meaningful interactions utilizing an active-matrix completion algorithm which allows the multi-perturbation interaction system 100 to avoid brute-force searches and intelligently select perturbation pairs based on a tradeoff between exploration (e.g., information gain) and exploitation (e.g., reward). In other words, the multi-perturbation interaction system 100 can significantly reduce the time, computational costs, and memory requirements of running upwards of 200 million experiments. Rather, the multi-perturbation interaction system 100 can selectively identify perturbation pairs with high potential for biological activity beyond that expected from the individual perturbations themselves.

Related to the accuracy and efficiency improvements, the multi-perturbation interaction system 100 further improves upon operational flexibility. Specifically, the multi-perturbation interaction system 100 expands the identification of meaningful biological interactions to pairwise perturbations (rather than just individual perturbations) and further searches a state space more efficiently by selecting perturbation pairs based on criteria that balances reward and information gain.

Figure 2:
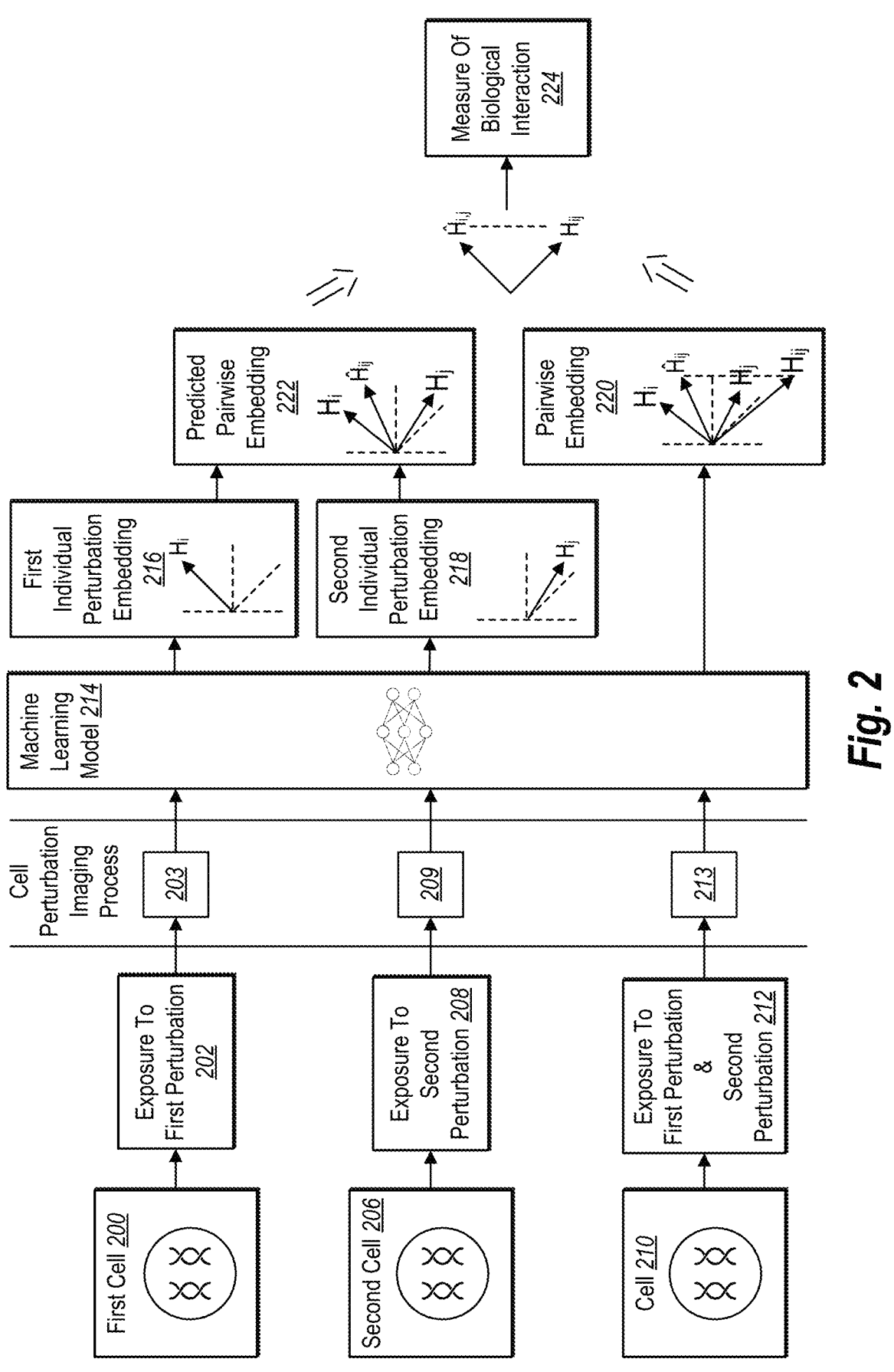
FIG. 2 illustrates an example diagram of the multi-perturbation interaction system generating a predicted pairwise embedding and a pairwise embedding to further generate a measure of biological interaction in accordance with one or more embodiments.

As mentioned above the multi-perturbation interaction system 100 utilizes a machine learning model to generate perturbation embeddings and further compare a predicted pairwise embedding with a pairwise embedding to generate a measure of biological interaction. FIG. 2 illustrates the multi-perturbation interaction system 100 combining individual perturbation embeddings to generate a predicted pairwise embedding for comparison with a pairwise embedding in accordance with one or more embodiments.

As shown in FIG. 2, the multi-perturbation interaction system 100 receives a first cell 200, a second cell 206, and a cell 210 (e.g., a third cell). As used herein, the term "cell" refers to a structural, functional, and biological unit of living organisms. Specifically, a cell can vary in size, shape, and function depending on the organism and the role of the cell. For example, a cell can include a plasma membrane to separate the internal cell environment from the external surroundings and the cell can further contain genetic material.

As shown in FIG. 2, the multi-perturbation interaction system 100 exposes the first cell 200 to a first perturbation 202, exposes the second cell 206 to a second perturbation 208, and exposes the cell 210 to a double perturbation 212 (e.g., the first perturbation 202 and the second perturbation 208). As shown, the multi-perturbation interaction system 100 utilizes a cell perturbation imaging process to capture perturbation images of the exposure to various perturbations. Specifically, FIG. 2 shows a first image 203 corresponding to the first cell 200 exposed to the first perturbation 202, a second image 209 corresponding to the second cell 206 exposed to the second perturbation 208, and a third image 213 corresponding to the cell 210 exposed to the double perturbation 212.

As used herein, the term perturbation images (or phenomic digital images), refers to a digital image portraying a cell (e.g., a cell after applying a perturbation). For example, a perturbation image includes a digital image of a stem cell after application of a perturbation and further development of the cell. Thus, a perturbation image comprises pixels that portray a modified cell phenotype resulting from a particular cell perturbation.

Moreover, as shown, the multi-perturbation interaction system 100 utilizes a machine learning model 214 to generate embeddings from the perturbation images. The multi-perturbation interaction system 100 embeds the perturbation images into a low dimensional feature space via the machine learning model 214 (e.g., a convolutional neural network or masked autoencoder) to generate perturbation image embeddings. As mentioned above, a perturbation embedding includes a feature vector generated by application of various convolutional neural network layers (at different resolutions/dimensionality). To illustrate, the multi-perturbation interaction system 100 utilizes the machine learning model 214 as described in UTILIZING MASKED AUTOENCODER GENERATIVE MODELS TO EXTRACT MICROSCOPY REPRESENTATION AUTOENCODER EMBEDDINGS, application Ser. No. 18/545,399 filed on Dec. 19, 2023 or UTILIZING MACHINE LEARNING MODELS TO SYNTHESIZE PERTURBATION DATA TO GENERATE PERTURBATION HEATMAP GRAPHICAL USER INTERFACES, U.S. patent application Ser. No. 18/526,707, filed Dec. 1, 2023, which are fully incorporated by reference herein.

As shown in FIG. 2, the multi-perturbation interaction system 100 utilizes the machine learning model 214 to generate a first individual perturbation embedding 216 from the first image 203 and a second individual perturbation embedding 218 from the second image 209. Further, from the first individual perturbation embedding 216 and the second individual perturbation embedding 218, the multi-perturbation interaction system 100 generates a predicted pairwise embedding 222.

For instance, the multi-perturbation interaction system 100 generates the predicted pairwise embedding 22 by determining a first normalized feature vector from the first individual perturbation embedding 216 and a control embedding and further determining a second normalized feature vector from the second individual perturbation embedding 218 and the control embedding. From combining the first normalized vector and the second normalized vector, the multi-perturbation interaction system 100 determines the predicted pairwise embedding for a first and second perturbation.

Specifically, the multi-perturbation interaction system 100 determines a first difference between the first individual perturbation embedding 216 and the control embedding and a second difference between the second individual perturbation embedding 218 and the control embedding. Moreover, the multi-perturbation interaction system 100 adds together the first difference and the second difference to arrive at the predicted pairwise embedding 222. As alluded to above, the control embedding refers to an embedding utilized to normalize an embedding (e.g., an embedding of a control experiment/cell without perturbations). In other words, the control embedding serves as a reference point for adjusting or scaling the embedding to additional data points.

In one or more embodiments, from the predicted pairwise embedding 222 and the pairwise embedding 220, the multi-perturbation interaction system 100 determines or generates a pairwise perturbation interaction score. As used herein, the term "pairwise perturbation interaction score" refers to a distance from the predicted pairwise embedding 222 to the pairwise embedding 220. Moreover, as shown, the pairwise perturbation interaction score indicates a measure of biological interaction 224. In some embodiments, the greater the pairwise perturbation interaction score, the more indicative it is of biological activity beyond that expected from the individual perturbations (e.g., knockouts) themselves.

Although FIG. 2 illustrates the first cell 200, the second cell 206, and the cell 210, it will be appreciated that the multi-perturbation interaction system 100 can operate with regard to a plurality of cells (e.g., a population of cells) in relation to each perturbation illustrated in FIG. 2 (e.g., cell wells that perturb a plurality of cells and capture a plurality of cell images). Thus, the multi-perturbation interaction system 100 can apply a first perturbation to a plurality of cells, develop the plurality of cells, and capture a plurality of images. Moreover, the multi-perturbation interaction system 100 can generate a plurality of perturbation embeddings. In some implementations, the multi-perturbation interaction system 100 generates individual perturbation embeddings (or pairwise embeddings) by combining (e.g., averaging or aggregating) the plurality of perturbation embeddings. Thus, for example, the multi-perturbation interaction system 100 can generate the first individual perturbation embedding 216 by aggregating a plurality of perturbation embeddings from a plurality of cells exposed to the first perturbation. Similarly, the multi-perturbation interaction system 100 can generate the second individual perturbation embedding 218 by aggregating a plurality of perturbation embeddings from a plurality of cells exposed to the second perturbation. Moreover, the multi-perturbation interaction system 100 can generate the pairwise embedding 220 by aggregating a plurality of perturbation embeddings from a plurality of cells exposed to the first perturbation and the second perturbation.

In addition, although FIG. 2 and various other embodiments herein describe utilizing an image of perturbed cells to generate a perturbation embedding, the multi-perturbation interaction system 100 can utilize a variety of cell representations to generate perturbation embeddings. As used herein, the term cell representation refers to a measurement or digital representation of cell features or characteristics. Thus, for example, a cell representation includes a digital image of a cell or other measurements of a cell. A cell representation can also include expression data indicating a particular expression in genes or other proteins (e.g., RNA, mRNA, etc.) resulting from a perturbation. To illustrate, a cell representation can include a count of genes and/or corresponding transcription proteins within a cell after exposure of the cell to one or more perturbations. The multi-perturbation interaction system 100 can utilize a variety of cell representations (e.g., image, protein measurement, chromatin measurement) with a machine learning model to generate a corresponding perturbation embedding.

Furthermore, although FIG. 2 illustrates the cell 210 as separate from the first cell 200 and the second cell 206, in some implementations the cell 210 may be the same as the first cell 200 or the second cell 206 (e.g., at different stages/times of being exposed to different perturbations). For example, the multi-perturbation interaction system 100 can apply a first perturbation to a particular cell, capture an image to generate the first individual perturbation embedding 216, and then apply a second perturbation to the particular cell, capture an additional image (after applying the second perturbation), and generate the pairwise embedding 220 from the additional image.

In one or more embodiments, the images (e.g., the first image 203, the second image 209, and the third image 213) can be described by a set of morphological features (e.g., in some embodiments, unknown morphological features), $$\{A_i\}_{i=1}^n,$$

that describe the presence or absence of observable morphological phenotypes. For example, if a cell is experiencing apoptosis (programmed cell death), observable characteristics include chromatin compaction and nuclear fragmentation, the appearance of apoptotic bodies, and blebbing (protruding cell membrane). If a cell is recycling cellular material in response to resource limitations (macroautophagy a.k.a. autophagy), the appearance of phagophores and autophagosomes are observable. In other words, each image exposed to perturbation includes a corresponding set of morphological features.

In one or more embodiments, the multi-perturbation interaction system 100 utilizes x to denote an indicator vector that records which genes have been knocked out in a given experiment, with $x_i=1$ if gene i is knocked out and 0 otherwise (e.g., gene i has not been knocked out). Each of the features depends on whether or not a subset of genes has been knocked out for any given experiment. Moreover, in some embodiments, the experiments are balanced such that $P(x_i)=P(x_j)$ for all i,j. In some embodiments, the multi-perturbation interaction system 100 utilizes unbalanced experiments by re-weighting the various gene knockout experiments. Accordingly, in some embodiments, the multi-perturbation interaction system 100 utilizes the following generative model:

$$A_i = f_i(x, \epsilon_i), \; P(A \mid x) = P(A_1, \ldots, A_n \mid x) = \prod_{i=1}^n P(A_i \mid x) \quad Y = g(A_1,$$

$$\ldots, A_n, \epsilon_y)$$

In the above notation, g is the observable function. In other words, the observable function includes a perturbation image (e.g., a microscopy image). In addition, the multi-perturbation interaction system 100 can treat g as a diffeomorphism (e.g., a mapping between differentiable manifolds that preserves smoothness and has a smooth inverse, in other words, a bijective (a one-to-one correspondence) and both g and the inverse of g are continuously differentiable). Further, in the above notation Y is the pixel level representation of the cell and $\epsilon_i$ and $\epsilon_y$ are noise variables assumed to be mutually independent. Moreover, from the generative process indicated in the above notation, the multi-perturbation interaction system 100 observes the image (Y), and x, the experimental description of which genes were knocked out.

In one or more embodiments, for a pair of genes (i and j), that influence an event $A_l$ (e.g., an event of cell death), the multi-perturbation interaction system 100 partitions the outcomes associated with each visual feature into mutually exclusive sets of events, each of which is a function of a single knockout. In particular, the multi-perturbation interaction system 100 represents the partitioning of outcomes associated with each visual feature as mutually exclusive sets of events as:

$$P(A_l \mid x_i, x_j) =$$

$$P\left(A_l^i \cup A_l^j \cup A_l^n \mid x_i, x_j\right) = P\left(A_l^i \mid x_i, x_j\right) + P\left(A_l^j \mid x_i, x_j\right) + P\left(A_l^N \mid x_i, x_j\right)$$

In some embodiments, the event $A_l$ denotes an event that cell l died. Further, the above notation indicates a partitioning of the set of states. For instance, as indicated in the above notation, one state can be when the cell dies from knocking out gene i and is responsible for cell l's death (e.g., indicated as $$A_l^i).$$

Further the above notation indicates an additional state where the cell dies from knocking out gene j, indicated as $$A_l^j.$$

Moreover, the above notation also indicates a state where the cell death does not result from knocking out either gene i or gene j, indicated as $$A_l^n.$$

In some embodiments, for any feature $A_l$, the multi-perturbation interaction system 100 assumes a lack of other effects, represented as:

$$i, j, P\left(A_l^i \mid x_i, x_j\right) = P\left(A_l^i \mid x_i\right)$$

The above notation indicates a formal statement of non-synthetic lethality. In other words, if the probability that a cell died when knocking out gene i was influenced by whether or not gene j was knocked out, then this would be an example of a synthetic lethal relationship.

Furthermore, for any feature $A_l$, the multi-perturbation interaction system 100 assumes a lack of off target effects, the multi-perturbation interaction system 100 represents this as:

$$i, j, P\left(A_l^n \mid x_i, x_j\right) = P\left(A_l^n\right)$$

The above notation rules out interactions between gene i and gene j among the other causes of the morphological feature.

In one or more embodiments, the multi-perturbation interaction system 100 utilizes embedding vectors to detect biological interactions. Specifically, the multi-perturbation interaction system 100 considers embedding vectors $h(\bullet)$, where the embedding vectors are constructed from the final hidden layer of a classifier. In some embodiments, the multi-perturbation interaction system 100 optimally trains the classifier such that $$P(x_i \mid Y) = \sigma\left(w_i^T h(Y)\right),$$

where $$\sigma := \frac{\exp(x_i)}{\sum_j \exp(x_j)},$$

which is the softmax function (e.g., an activation function to convert numerical values into probabilities). Moreover, during training, the multi-perturbation interaction system 100 utilizes sufficiently diverse labels to ensure that the representation is identified up to a linear transformation. For instance, the multi-perturbation interaction system 100 utilizes a trained classifier where $h_i := E[h(Y) \mid x_i = 1] - E[h(Y) \mid x = 0]$ is the average of the embeddings associated with a particular knockout centered around a control embedding (e.g., control wells).

In one or more embodiments, given the above notations, the multi-perturbation interaction system 100 determines that the sum of the individual perturbation embeddings is equal to the pairwise embedding, indicated as:

$$h_i + h_j = h_{i,j}$$

In other words, the above notation indicates that non-interaction between genes imply that the multi-perturbation interaction system 100 can add single gene embeddings and predict the pairwise embedding. In addition to predicting the embedding that would be derived from an experiment without running it, the multi-perturbation interaction system 100 further utilizes prediction failures (e.g., where the sum of the individual perturbation embeddings is not equal to the pairwise embedding) to detect when synthetic-lethal-style interactions or other morphological changes occur strictly from a double perturbation (e.g., a double gene knockout). As is described in additional detail below (e.g., FIGS. 3-5), the multi-perturbation interaction system 100 further utilizes the prediction failure scores (e.g., the measure of biological interaction 224) to identify candidate perturbation pairs with a high potential for meaningful interactions resulting from double perturbations.

As mentioned above, with the measures of biological interaction, the multi-perturbation interaction system 100 can further reduce the problem of identifying promising perturbation pairs to active learning. For instance, active learning can include active matrix completion, uncertainty sampling (e.g., prioritizing selections within a matrix that skew towards maximizing information gain), density-based methods (e.g., selecting data points that are under-represented or have a high data density to prioritize comprehensively exploring a state space), and expected model change (e.g., generating a prediction for how much a model will change if a particular data point is labeled i.e., tested to obtain actual data).

Figure 3:
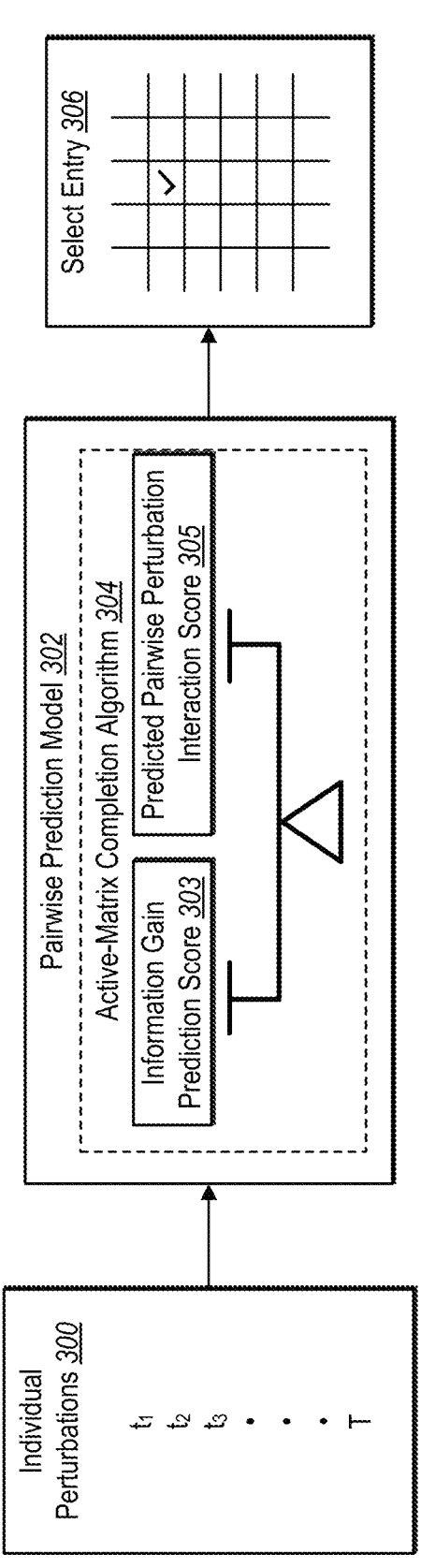
FIG. 3 illustrates an example diagram of the multi-perturbation interaction system utilizing a pairwise prediction model to select an entry from a matrix for further exploration in accordance with one or more embodiments.

In one or more embodiments, the multi-perturbation interaction system 100 reduces the problem of identifying promising perturbation pairs to an active-matrix completion problem, which avoids the need for brute-force searches. FIG. 3 illustrates the multi-perturbation interaction system 100 utilizing a pairwise prediction model 302 to select an entry from a matrix. As used herein, a "matrix" refers to an array (e.g., a two-dimensional array arranged in rows and columns). Specifically, the matrix includes rows with a set of perturbations and columns with an additional set of perturbations. Moreover, the matrix includes entries corresponding to a specific pair of perturbations. For example, a specific entry of the matrix can refer to a measure of biological interaction for a specific double gene knockout for a cell.

In one or more embodiments, the multi-perturbation interaction system 100 generates a matrix for pairs of perturbations. Specifically, the pairs of perturbations can include different pairs of gene knockouts. Furthermore, the matrix generated by the multi-perturbation interaction system 100 includes the pairwise perturbation experiment data plus individual perturbation data that lacks pairwise experimentation data. In other words, the matrix models the state space for perturbation pairs and includes both entries for measures of biological interaction for actual pairwise perturbations and predictions of measures of biological interactions for individual perturbations without actual pairwise perturbation data.

As shown in FIG. 3, the multi-perturbation interaction system 100 receives individual perturbations 300 (and/or pairwise perturbations from already conducted experiments). As used herein, the "pairwise prediction model" refers to a model that the multi-perturbation interaction system 100 utilizes to select an entry from the matrix. Specifically, the pairwise prediction model 302 generates a plurality of predicted pairwise perturbation interaction scores for entries of the matrix and balances that with corresponding information gain prediction scores to perform an active-matrix completion technique (e.g., which selects an entry from the matrix).

As used herein a "predicted pairwise perturbation interaction score" refers to a prediction for a perturbation pair (e.g., in the matrix) regarding a perturbation interaction score. In other words, the multi-perturbation interaction system 100 generates a prediction of reward for a perturbation pair, where the multi-perturbation interaction system

100 only has access to single perturbation data for that perturbation pair. For instance, the multi-perturbation interaction system 100 has access to a plurality of individual perturbation embeddings (e.g., including the perturbation pair), but does not have data for exposing a cell to a specific set of double perturbations. As such, the multi-perturbation interaction system 100 utilizes the pairwise prediction model to generate the predicted pairwise perturbation interaction score.

As used herein, an "information gain prediction score" refers to an indication of the amount of increase in knowledge or reduction in uncertainty. Specifically, the multi-perturbation interaction system 100 generates an information gain prediction score based on an entropy measure, represented as a probability distribution. For example, the multi-perturbation interaction system 100 references existing knowledge (e.g., the plurality of pairwise perturbations and the corresponding measures of biological interactions) to determine the information gain prediction score for a particular perturbation pair. To illustrate, a higher information gain prediction score indicates that if selected, the entry is more informative and valuable for reducing uncertainty.

As shown in FIG. 3, based on an information gain prediction score 303 (e.g., a corresponding information gain prediction) and a predicted pairwise perturbation interaction score 305, the multi-perturbation interaction system 100 utilizes an active-matrix completion algorithm 304 to select an entry 306. As used herein, the term "active-matrix completion algorithm" refers to actively selecting and acquiring certain entries of an incomplete matrix to efficiently fill in or predict the missing values. Specifically, the matrix includes as entries a plurality of pairwise perturbations and corresponding measures of biological interactions (e.g., already performed double perturbations) and the incomplete entries correspond with perturbation pairs without pairwise perturbations already performed (e.g., the multi-perturbation interaction system 100 only has access to individual perturbation data). As mentioned, the multi-perturbation interaction system 100 utilizes the active-matrix completion algorithm 304 to select one or more incomplete entries based on a balance between the information gain prediction score 303 and reward (e.g., the predicted pairwise perturbation interaction score 305).

As illustrated, the multi-perturbation interaction system 100 utilizes the active-matrix completion algorithm 304 to select the entry 306 from the matrix. As used herein, the term "perturbation pair" refers to a pair of perturbations (e.g., gene knockouts, compounds, or a gene knockout-compound pair) corresponding to an entry of the matrix. Specifically, the multi-perturbation interaction system 100 has not performed experimentation of exposing a cell to the perturbation pair corresponding to the matrix entry.

The following description provides additional details of efficiently discovering interacting perturbation pairs (e.g., gene pairs). As discussed above in FIG. 2, the multi-perturbation interaction system 100 utilizes the measure of biological interaction (e.g., the prediction error or loss) as an indicator of potential perturbation pair interactions (e.g., gene interactions). In some embodiments, the multi-perturbation interaction system 100 identifies gene-pair knockouts that induce large interactions (e.g., a large measure of biological interaction) in order to discover additional gene-gene relationships within the constraints of only having a fixed number of experimental resources (e.g., performing double gene knockouts on all pairs is unfeasible).

As alluded to above, in one or more implementations the multi-perturbation interaction system 100 reduces the problem of discovering additional interacting gene pairs efficiently to a matrix completion framework. For instance, the multi-perturbation interaction system 100 utilizes X to denote the space of possible experiment designs, which is a set of tuples G×G where G is the set of genes, each associated with a reward score R: X→$\mathbb{R}$. For instance, the reward for pair (i,j)∈ G×G is defined as follows:

$$R(i, j) := (\mathbb{E}[h_{i,j} - h_i - h_j])^2 \text{ where } h_i := E[h(Y) \mid x_i - 1] - E[h(Y) \mid x = 0]$$

In the above notation, the matrix is symmetric as the reward function is invariant to the order of the perturbations.

Specifically, the multi-perturbation interaction system 100 utilizes a framework of adaptive sampling for discovery with information directed sampling. For instance, adaptive sampling for discovery refers to a sequential decision-making problem that chooses entries/points that yield information to improve a model estimate. Furthermore, information directed sampling refers to an optimization approach that balances exploration and exploitation while learning from partial feedback. To illustrate, the multi-perturbation interaction system 100 implements the methods described in Ziping xu, Eunjae shim, Ambuj Tewari, and Paul Zimmerman, *Adaptive Sampling for Discovery*, arXiv: 2205.14829v3, 2022 and Daniel Russo and Benjamin Van Roy, *Learning to Optimize Via Information-Directed Sampling*, arXiv: 1403.5556v7, 2017, which are both fully incorporated by reference herein.

In one or more embodiments, the multi-perturbation interaction system 100 formalizes a problem of selecting an entry from a matrix as a sequential Bayesian optimal experimental design, described in E. G. Ryan, C. C. Drovandi, J. M. McGree, and A. N. Pettitt, *A review of modern computational algorithms for Bayesian optimal design*, International Statistical Review, 84(1):128-154, 2016, A. Foster, *Variational, Monte Carlo and policy-based approaches to Bayesian experimental design*, PhD thesis, University of Oxford, 2021, and T. Rainforth, A. Foster, D. R. Ivanova, and F. B. Smith, *Modern Bayesian experimental design*, arXiv preprint arXiv: 2302.14545, 2023, which is incorporated herein by reference in its entirety. In such an experiment, the experiments x∈X is designed with outcomes y∈ Y governed by a generative process y~p(y|γ,x) with parameters γ. In some embodiments, the experiments are performed sequentially ($x_1$ . . . , $x_T$) with the objective of maximizing a measure of utility, e.g., the information gain. In other words, the multi-perturbation interaction system 100 iteratively selects entries from a matrix that indicate the highest potential information gain. For instance, the multi-perturbation interaction system 100 represents the Bayesian optimal experimental design as:

$$x_t^* = \frac{\arg\max MI(\gamma, \{x, y\} \mid D^t)}{x \in \{X \backslash D_x^t\}}$$

In the above notation, $$x_t^*$$

denotes an optimal solution for running an experiment from the set of entries, which is equivalent to an arg max operation that finds the input that maximizes a function of maximizing the mutual information between an experimental outcome and a parameter of interest (e.g., parameters $\gamma$). Further, the above notation indicates that x is an element of the set of elements that are in set X but not in set $$D_x^t,$$

where $D^t$ indicates a dataset of observed data (e.g., the plurality of pairwise perturbations and the corresponding measures of biological interaction).

In some embodiments, the multi-perturbation interaction system 100 solves an optimization problem (of acquiring the most information in an efficient manner) by estimating a posterior probability $p(\gamma|D_i)$ and knowledge of the generative process $p(y|\gamma,x)$ and nested integral over y and $\gamma$ which can suffer from poor convergence rates when estimated from samples. Accordingly, the multi-perturbation interaction system 100 utilizes the above methods to search over a combinatorial space of sets of experiments (e.g., perturbation pairs) to be selected at each step.

In one or more embodiments, the multi-perturbation interaction system 100 further implements a multi-armed bandits framework as described in W. R. Thompson, *On the likelihood that one unknown probability exceeds another in view of the evidence of two samples*, Biometrika, 25(3-4):285-294, 1933, H. Robbins, *Some aspects of the sequential design of experiments*, 1952, and T. Lattimore and C. Szepesvari, *Bandit algorithms*, Cambridge University Press, 2020. For instance, the multi-armed bandits framework includes learning a policy $\Pi$ which maps a history of observations (e.g., the measures of biological interactions for the comparison between actual pairwise embeddings and predicted pairwise embeddings) to a distribution over a set of possible actions (A), where each action $a \in$ A is associated with an unknown potentially stochastic reward $f(a)$, such that after T actions sampled from the policy $(a_1 \ldots, a_T)$ the regret $$R_T = T \max_{a \in A} \mathbb{E}[f(a)] - \sum_i^T f(a_i)$$

is minimized. In other words, the regret bounds for bandit optimization are characterized in terms of information gain.

In one or more embodiments, the multi-perturbation interaction system 100 denotes the set of possible distributions defined over X by D(X), the history of actions and their corresponding rewards until round t by $$H_t = ((x_k, R(x_k)))_{k=1}^{t-1}$$

and $X_t$ denotes the set of available designs at round t. For instance, the policy $\Pi_{IDs}$ (e.g., information directed sampling policy) is defined as a map from $H_t$ to $D(X_t)$. Further, for a discrete space of actions, each element of $D(X_t)$ is a vector which represents the distribution over available actions. Specifically, the multi-perturbation interaction system 100 defines an instant regret of taking an action as $\Delta_t(x) = \mathbb{E}_{f \sim p(R|H_t)}[\max_{x' \in x_t} f(x') - f(x)]$, where the expectation is over samples from the posterior over the reward function $f$ given the history of observations $H_t$. Additionally, the multi-perturbation interaction system 100 defines $$g(x) = MI\big(X_{t,1}^*, \ldots, X_{t,T-t+1}^*; R(X_t)|H_t, X_t = x\big)$$

as the information gain about the top T−t+1 unselected actions. Further the information directed sampling policy at round t can be computed by minimizing the information ratio:

$$\pi_{IDS} \in^{arg\,min\,\Psi_{\pi,t}:=} \frac{(\Delta_t^T \pi)^\lambda}{g_t^T \pi}$$

$$\pi \in D(X_t)$$

In the above notation, $\lambda$ controls the tradeoff between lower instant regret (exploitation) and higher information gain (exploration). For instance, the multi-perturbation interaction system 100 relies on an approximate algorithmic choice, replacing $g_t$ with a conditional variance $$v_t(x) = Var_t(\mathbb{E}[R(X_t)|X_1^*, X_t = x]),$$

as it is lower bound on the information gain $g_t(x) \geq v_t(x)$. Furthermore, the multi-perturbation interaction system 100 adopts low-rank matrix with a prior of row and column spaces being sampled from a standard Gaussian. In particular, to obtain samples from the posterior distribution over the low-rank (where m is the rank) reward matrix, the multi-perturbation interaction system 100 utilizes a stochastic variational inference, described in D. Wingate and T. Weber, *Automated variational inference in probabilistic programming*, arXiv preprint arXiv: 1301.1299, 2013, R. Ranganath, S. Gerrish, and D. Blei, Black Box variational inference, In *Artificial intelligence and statistics*, pages 814-822, PMLR, 2014, J. Bradbury, R. Frostig, P. Hawkins, M. J. Johnson, C. Leary, D. Macalurin, G. Necula, A. Paszke, J. VanderPlas, S. Wanderman0Milne, and Q. Zhang, *JAX: composable transformations of Python+NumPy programs*, 2018, and E. Bingham, J. P. Chen, M. Jankowiak, F. Obermeyer, N. Pradhan, T. Karaletsos, R. Singh, P. A. Szerlip, P. Horsfall, and N. D. Goodman, *Pyro: Deep universal probabilistic programming*, J. Mach. Learn. Res., 20:28:1-28:6, 2019, and D. Phan, N. Pradhan, and M. Jankowiak, *Composable effects for flexible and accelerated probabilistic programming in numpyro*, arXiv preprint arXiv: 1012.11554, 2019.

In some embodiments, the multi-perturbation interaction system 100 utilizes the following algorithm for adaptive sampling for discovery for designing gene pair knockouts:

```
1:    Initialize H₁ = { }
2:    for t = 1 . . . ., T do
3:        Estimate posterior p(R| Hₜ)
4:        Compute information ratio Ψₜ
5:        Pick batch (x₁, . . . .,xᵦ) greedily which minimize Ψₜ
6:        Perform experiments and compute R(x)
7:        Update Hₜ₊₁ = Hₜ ∪ {xₜ¹, R(xₜ¹), ... ,(xₜᵇ, R(xₜᵇ))}
8:    end for
```

For instance, the above algorithm indicates that for adaptive sampling for discovery, the multi-perturbation interaction system 100 initializes the history of observations for a first perturbation pair to T (e.g., the last perturbation pair observed) and sequentially from 1 to T, the multi-perturbation interaction system 100 estimates a posterior distribution (e.g., which indicates a posterior probability of the reward given the specific instance of observation). Furthermore, the multi-perturbation interaction system 100 computes the information ratio for the specific instance (e.g., t . . . T) and picks a batch from ($x_1$, . . . , $x_b$), which indicates the available perturbation pairs for selection. Moreover, as indicated, the multi-perturbation interaction system 100 performs experiments for the selected perturbation pair and computes the actual measure of biological interaction. From the computed actual measure of biological interaction, the multi-perturbation interaction system 100 can update the matrix e.g., or the history of observations.

Figure 4:
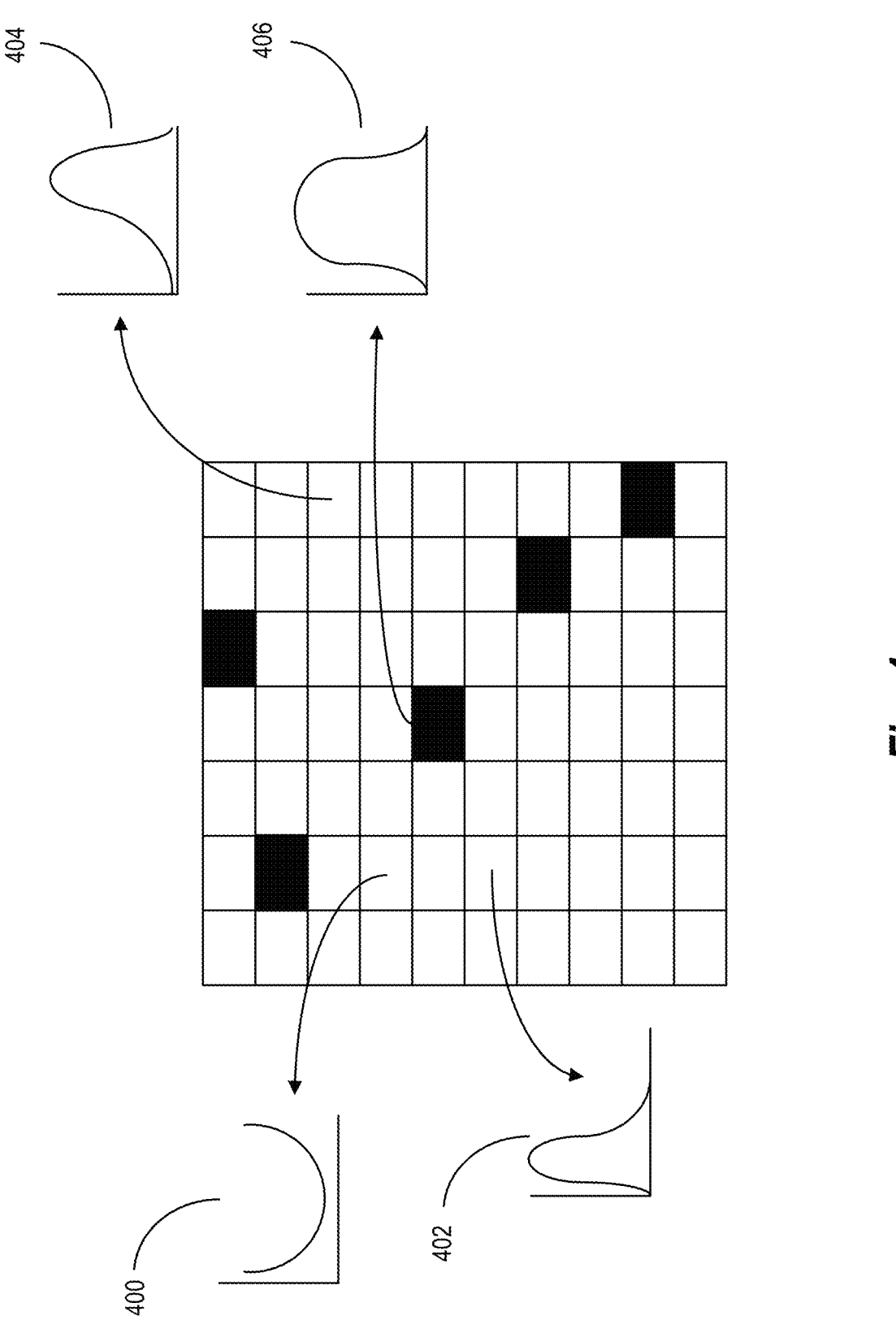
FIG. 4 illustrates an example diagram of a matrix that includes multiple measures of biological interaction and a plurality of predicted pairwise perturbation interaction scores in accordance with one or more embodiments.

FIG. 4 illustrates a matrix with various entries and corresponding probability distributions treated as reward in accordance with one or more embodiments. For example, FIG. 4 shows a first entry with a first probability distribution 400, a second entry with a second probability distribution 402, a third entry with a third probability distribution 404, and a fourth entry with a fourth probability distribution 406. For instance, FIG. 4 shows the fourth entry as filled in (e.g., shaded), which indicates that it is for a perturbation pair where a pairwise perturbation experiment has already been performed.

As shown in FIG. 4, the various probability distributions represent a posterior over an error. Specifically, the posterior refers to a posterior distribution (e.g., Bayesian) that represents the updated probability about a predicted pairwise perturbation interaction score in view of observed data (e.g., the pairwise perturbation interaction score which indicates the measure of biological interaction). In other words, FIG. 4 illustrates a probabilistic estimate of potential errors (e.g., the predicted pairwise perturbation interaction scores) for the plurality of perturbation pairs (e.g., as predicted by the pairwise prediction model). Accordingly, FIG. 4 shows the probability distributions, which provides a distribution of possible interaction scores (e.g., reward) and represents the uncertainty and reliability of the prediction (e.g., the information gain).

To illustrate, FIG. 4 shows that the first probability distribution 400 indicates uncertainty in the reliability of a prediction, namely that a selection of the entry corresponding to the probability distribution 400 could be high error (e.g., a meaningful interaction indicated by the large scalar difference between the combination of the individual perturbation embeddings and the actual pairwise perturbation embedding) or a low error (e.g., an interaction that does not deviate from the normal assumptions of combining individual perturbations). Further, the second probability distribution 402 shows low error at a probability below 0.5, the third probability distribution 404 shows high error at a probability above 0.5, and the fourth probability distribution shows a high error (e.g., at approximately 0.5).

Moreover, as discussed in FIG. 3, the multi-perturbation interaction system 100 utilizes the pairwise prediction model to generate the probability distribution shown for each entry of the matrix, where the probability distribution indicates reward (e.g., by the error) and information gain (e.g., via the uncertainty or reliability of the prediction). Furthermore, the multi-perturbation interaction system 100 utilizes the active-matrix completion algorithm to select an entry from the matrix for initiating downstream experimentation. Thus, for instance, the multi-perturbation interaction system 100 can select the entry corresponding to the first probability distribution 400 (e.g., utilizing the active-matrix completion algorithm) due to the high information gain potential (e.g., uncertainty as to whether the perturbation pair is high reward or low reward).

Figure 5:
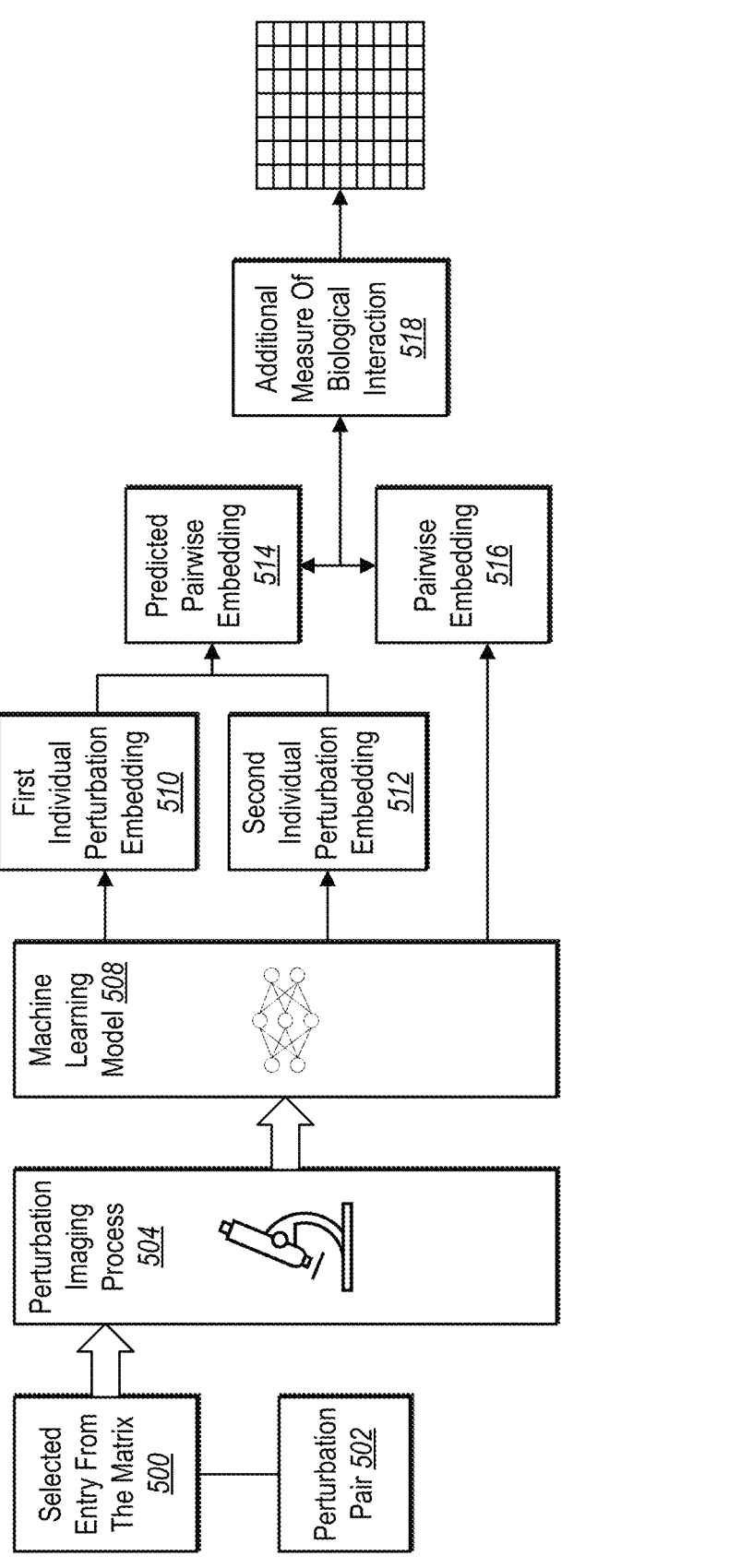
FIG. 5 illustrates an example diagram of the multi-perturbation interaction system initiating downstream experimentation for a perturbation pair that corresponds with a selected entry from the matrix in accordance with one or more embodiments.

As mentioned above, the multi-perturbation interaction system 100 can select an entry from the matrix that corresponds to a perturbation pair and initiate one or more additional downstream experiments for the perturbation pair. FIG. 5 illustrates the multi-perturbation interaction system 100 initiating downstream experimentation and generating an additional measure of biological interaction in accordance with one or more embodiments.

FIG. 5 shows the multi-perturbation interaction system 100 transmitting a perturbation pair 502 corresponding to an entry 500 from the matrix to initiate additional experimental processes for generating an additional measure of biological interaction 518 for the perturbation pair. Specifically, FIG. 5 shows the multi-perturbation interaction system 100 performing a perturbation imaging process 504 on the perturbation pair 502. For instance, the perturbation imaging process 504 for the perturbation pair 502 includes exposing a cell to the perturbation pair 502 (e.g., a specific double gene knockout as indicated by the entry in the matrix) and imaging the cell exposed to the perturbation pair 502. Furthermore, as shown, the multi-perturbation interaction system 100 utilizes a machine learning model 508 to process the images of the cell exposed to the perturbation pair 502 to generate various embeddings.

As shown, the multi-perturbation interaction system 100 utilizes the machine learning model 508 to generate a first individual perturbation embedding 510 corresponding to a perturbation from the perturbation pair 502 and a second individual perturbation embedding 512 corresponding to the other perturbation from the perturbation pair 502. For instance, the multi-perturbation interaction system 100 generates the individual perturbation embeddings from exposing cells to the perturbations individually (e.g., not in combination). Moreover, as shown, the multi-perturbation interaction system 100 generates a predicted pairwise embedding 514 from combining the first individual perturbation embedding 510 and the second individual perturbation embedding 512.

Additionally, the multi-perturbation interaction system 100 generates a pairwise embedding 516 from a cell being exposed to the perturbation pair 502. As shown, the multi-perturbation interaction system 100 compares the pairwise embedding 516 (e.g., the actual embedding resulting from exposing a cell to the perturbation pair 502) with the predicted pairwise embedding 514 (e.g., the predicted embedding resulting from individually exposing cells to perturbations). From the comparison, the multi-perturbation interaction system 100 generates an additional pairwise perturbation interaction score which indicates the additional measure of biological interaction 518.

As further shown, the multi-perturbation interaction system 100 utilizes the additional measure of biological interaction 518 and updates the matrix (e.g., discussed in FIGS. 3-4) to include the additional measure of biological interaction 518 for the perturbation pair 502. As discussed above in FIGS. 3 and 4, the multi-perturbation interaction system 100 selects an entry from the matrix that corresponds to a perturbation pair, based on a balance between information gain and the reward (e.g., the predicted pairwise perturbation interaction score). Thus, FIG. 5 illustrates the multi-perturbation interaction system 100 further testing the entry to determine the actual measure of biological interaction (e.g., the distance between the actual pairwise embedding and the predicted pairwise embedding). Accordingly, the multi-perturbation interaction system 100 updates the matrix to include the actual measure of biological interaction.

In one or more embodiments, after updating the matrix to include the additional measure of biological interaction 518, the multi-perturbation interaction system 100 further performs the acts and processes discussed above in FIGS. 3-4. Specifically, the multi-perturbation interaction system 100 utilizes the pairwise prediction model to generate the predicted pairwise perturbation interaction scores and the information gain prediction scores based on the updated matrix. For example, the multi-perturbation interaction system 100 utilizes the active-matrix completion algorithm to further select an additional entry from the matrix to initiate downstream experimentation with the same principles discussed in FIG. 5. Accordingly, the multi-perturbation interaction system 100 iteratively updates the matrix, generates updated predictions, and initiates downstream experimentation in an efficient manner to explore the state space (e.g., without performing brute force searches).

Figure 6:
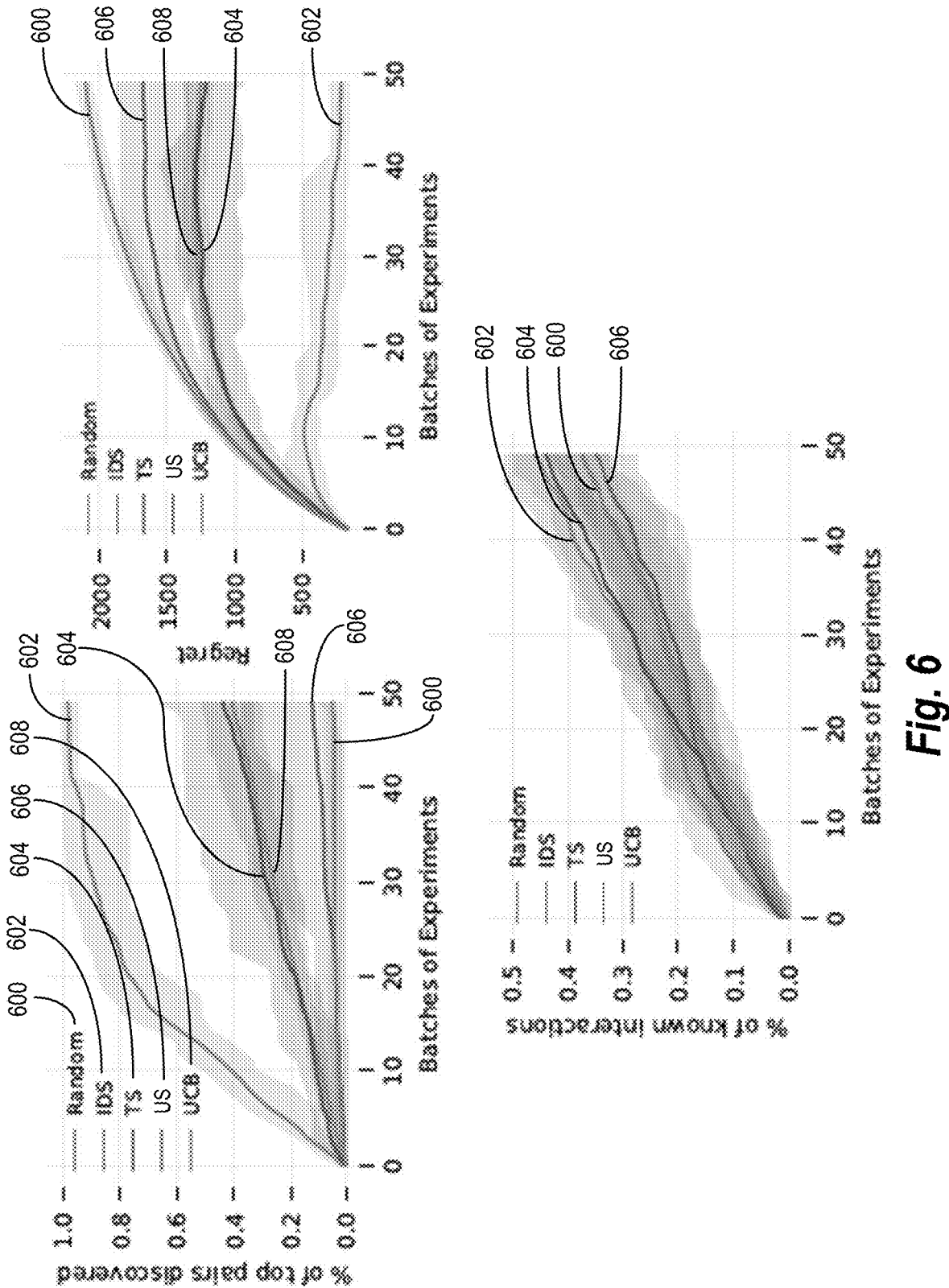
FIG. 6 illustrates example experimental results of an experimental implementation of the multi-perturbation interaction system in accordance with one or more embodiments.

As mentioned above, the multi-perturbation interaction system 100 more efficiently searches the state space as compared to other approaches, without having to resort to brute-force searching techniques. FIG. 6 illustrates an example implementation of the multi-perturbation interaction system 100 outperforming other approaches in discovering perturbation pairs with meaningful interactions (e.g., interactions beyond that expected from individual perturbations) utilizing a new benchmark task for in-silico validation. In one or more embodiments, experimenters tested the multi-perturbation interaction system 100 by collecting a benchmark dataset of all pairs of gene knockouts for 50 genes in HUVEC cells (e.g., human umbilical vein endothelial cells) with three CRISPR guides per gene (e.g., clustered regularly interspaced short palindromic repeats, which allows experimenters to make precise changes to DNA).

For instance, experimenters ran experiments with embeddings from a DenseNet-based classifier described in G. Huang, Z. Liu, L. Van Der Maaten, and K. Q. Weinberger, *Densely connected convolutional networks*, in Proceedings of the IEEE conference on computer vision and pattern recognition, pages 4700-4708, 2017. The experimenters train the DenseNet-based classifier on an rxrx1 dataset described in M. Sypetkowski, M. Rezanejad, S. Saberian, O. Kraus, J. Urbanik, J. Taylor, B. Mabey, M. Victors, J. Yosinski, A. R. Sereshkeh, et al., *Rxrx1: A dataset for evaluating experimental batch correction methods*, in Proceedings of the IEEE/CVF Conference on Computer Vision and Pattern Recognition, pages 4284-4293, 2023. In some embodiments, the experimenters average the generated embeddings across all guides and replicates, resulting in 1225 pairwise gene embeddings which form an 'unknown' target $h_{i,j}$ and 50 single gene embeddings $h_i$, which are assumed to be known at the start of an active learning experiment.

As shown in FIG. 6, the experimenters measure an experimental implementation of the multi-perturbation interaction system 100 (e.g., IDS 602) against random 600 (e.g., a random policy of selection), TS 604 (e.g., Thompson Sampling, which includes an agent maintaining a probability distribution over expected rewards for each action such that the agent at each step samples from these distributions and selects the action with the highest sampled reward), US 606 (e.g., uncertainty sampling, which includes an algorithm to select instances with high uncertainty, in other words uncertainty sampling skews towards information gain), and UCB 608 (e.g., Upper Confidence Bound, which includes an algorithm that balances exploration and exploitation by estimating the upper confidence bound of the expected reward for each action and selecting the action with the highest upper confidence bound).

FIG. 6 illustrates three graphs, where the top left graph is the percentage of top pairs discovered over 50 batches of experiments. Specifically, the top left graph indicates experimenters looking to a fraction of the pairs with the top 5 percentile of scores recovered by the algorithm capturing the ability to explore the high scoring regions. Further, the top right graph is the regret experienced by each method. Specifically, the top right graph shows an evaluation of the regret of each algorithm with respect to an optimal policy with access to the score matrix (e.g., the reward matrix shown below in FIG. 7) to acquire the highest scoring pairs at each round. Lastly, the bottom middle graph is the performance of each method for known interactions. In other words, the bottom middle graph illustrates the number of known biological relations and how many each method is able to recover.

Experimenters found that the experimental implementation for the multi-perturbation interaction system 100 discovered pairs of genes that result in large norm interactions (e.g., biological activity beyond that expected from the individual knockouts themselves) significantly faster than random search, giving a 10% increase in the number of biological interactions that experimenters were able to discover after 50 rounds of experimentation. The relationships that experimenters detected were also complementary to that which would have been discovered using just single perturbations, and as a result, the two approaches can be combined to get a more detailed estimate of the relationships between genes from perturbation experiments.

As shown in FIG. 6, the solid lines represent the mean performance, whereas the shaded region represent all the runs (min-max). As illustrated by FIG. 6, the multi-perturbation interaction system 100 outperforms all the baselines significantly in terms of top scoring pairs discovered. Specifically, the top left graph illustrates that the multi-perturbation interaction system 100 discovers all the pairs with the top-5 percentile scores, whereas all the baselines barley recovers half of the top pairs.

Further, the multi-perturbation interaction system 100 outperforms other methods in terms of regret (e.g., cumulative difference between the performance of a model and the performance of the best possible action of the model in hindsight). In terms of regret, the multi-perturbation interaction system 100 outperforms the baselines, with the random method performing the worst. For instance, the top left graph demonstrates that the multi-perturbation interaction system 100 is able to exploit the low-rank structure in the reward matrix effectively.

In terms of known interactions, the multi-perturbation interaction system 100 still outperforms the baselines. As shown in the bottom middle graph for known interactions, the performance of all methods is quite similar, however the multi-perturbation interaction system 100 and the TS 604 outperform all the baselines recovering around 10% more known relations.

Figure 7:
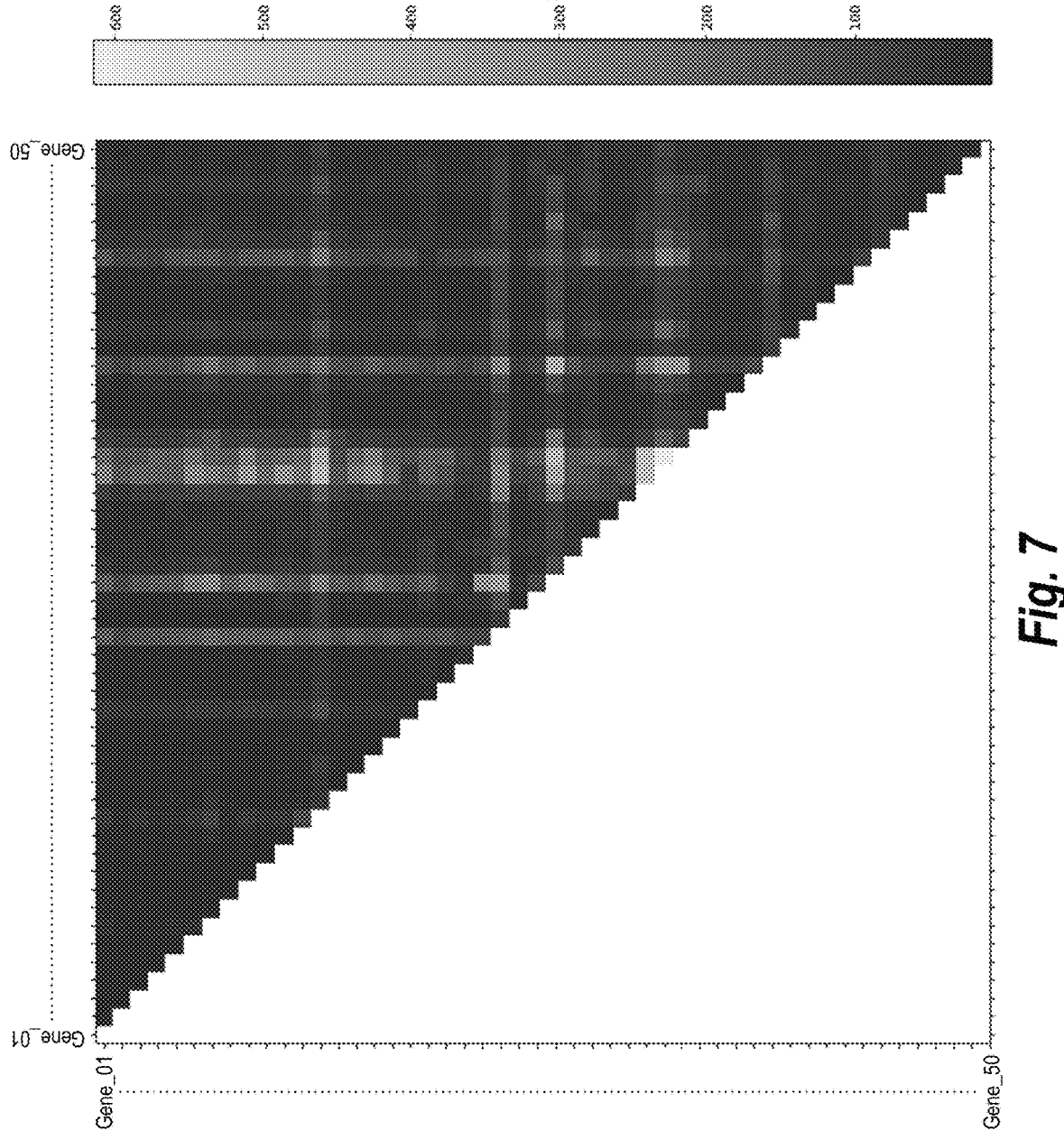
FIG. 7 illustrates a reward matrix for a set of fifty genes in accordance with one or more embodiments.

As mentioned above, FIG. 7 illustrates a reward matrix in accordance with one or more embodiments. Specifically, for the set of 50 genes selected with a bias towards genes with known gene-gene interactions, FIG. 7 illustrates the final reward (e.g., the interaction scores) for 1225 pairwise gene embeddings. FIG. 7 illustrates a scale on the right side of the graph, indicated as R(i,j). Specifically, R(i,j) is the reward for each pair, where the darker the shade the lower reward (e.g., bottom of the scale) and the lighter the shade the higher the reward (e.g., top of the scale). Accordingly, FIG. 7 illustrates an example embodiment of the multi-perturbation interaction system 100 generating a matrix for perturbation pairs and utilizing active-matrix completion techniques to select an entry from the matrix based on a predicted reward. Furthermore, as mentioned, the multi-perturbation interaction system 100 initiates downstream experimentation on a selected perturbation pair, determines a measure of biological interaction for the selected pair, and updates the matrix to include the actual measure of biological interaction. In doing so, the multi-perturbation interaction system 100 iteratively fills in entries of the reward matrix by selecting an entry based on the predicted reward and information gain.

Figure 8:
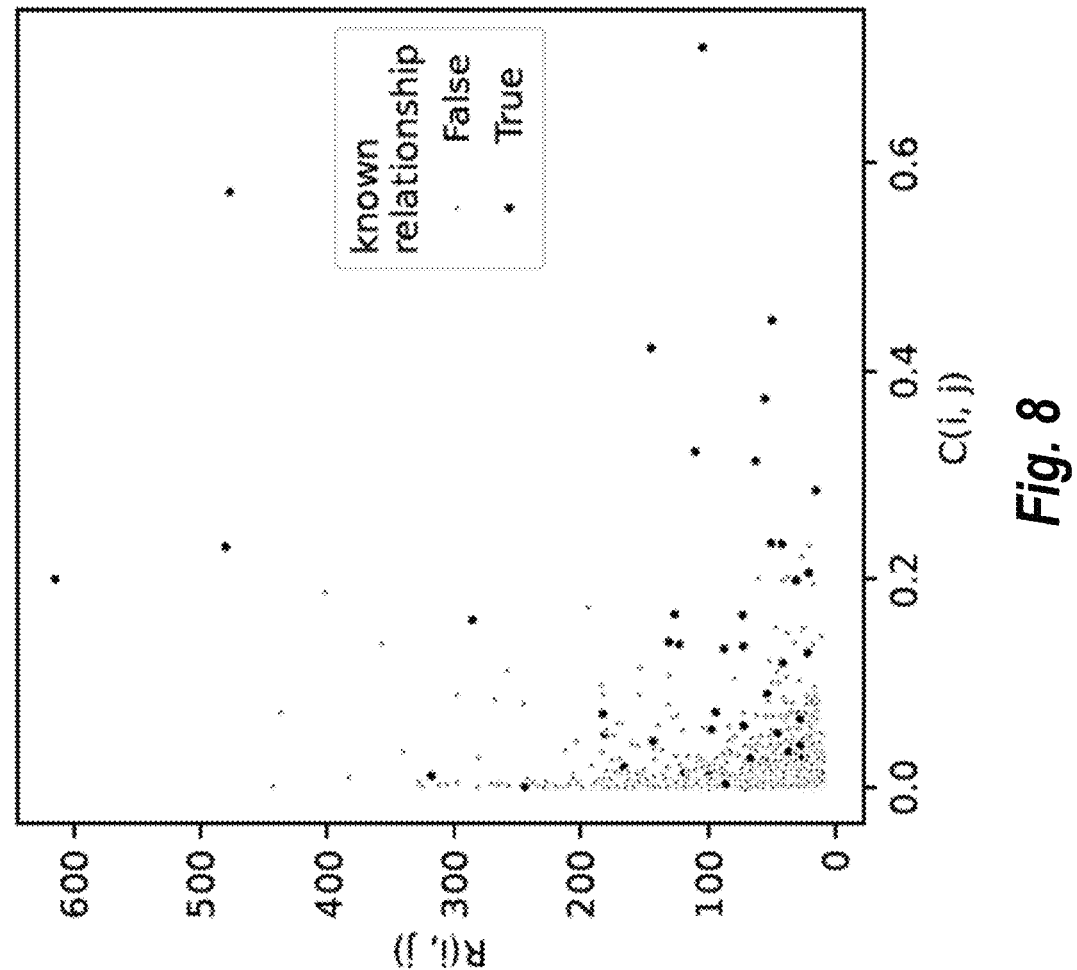
FIG. 8 illustrates experimental results comparing a cosine similarity with the measure of biological interaction in accordance with one or more embodiments.

As alluded to above, the multi-perturbation interaction system 100 utilizes a high measure of biological interaction (e.g., a high score relative to an established threshold) to determine whether independence assumptions (e.g., biological activity beyond that expected from the individual knockouts themselves) are violated in a biologically meaningful way that is indicative of biological interactions. Furthermore, in some embodiments, a high measure of biological interaction is complementary to a squared cosine similarity (e.g., $C(i,j):=\cos(w_i, w_j)^2$). Cosine similarity is a metric utilized for inferring biological relationships as described in N. Moshkov, M. Bornholdt, S. Benoit, M. Smith, C. McQuin, A. Goodman, R. A. Senft, Y. Han, M. Babadi, P. Horvath, et al., *Learning representations for image-based profiling of perturbations*, Biorxiv, pages 2022-08, 2022 and O. Kraus, K. Kenyon-Dean, S. Saberian, M. Fallah, P. McLean, J. Leung, V. Sharma, A. Khan, J. Balakrishnan, S. Celik, et al., *Masked autoencoders are scalable learners of cellular morphology*, arXiv preprint arXiv: 2309.16064, 2023. In FIG. 8 the cosine similarity is squared to simplify the comparison between metrics.

FIG. 8 illustrates plotting both the reward (e.g., the measure of biological interaction determined by comparing the predicted pairwise embedding with the actual pairwise embedding) and the cosine similarity for all pairs of genes. As shown by the key in FIG. 8, the darker shaded dots represent known relationships between genes and the lighter shaded dots indicated unknown relationships between genes. As shown, the known relationships amount to the highest values for each metric, and the metrics are complementary and not merely overlapping.

Moreover, as mentioned, the lighter shaded dots indicate unknown relationships between genes. In some instances, the multi-perturbation interaction system 100 identifies gene pairs with meaningful interactions (e.g., beyond that expected from individual knockouts) that are poorly studied or not studied at all in the scientific literature. Furthermore, to reiterate, many of the pairwise interactions identified by the multi-perturbation interaction system 100 include interactions beyond programmed cell death and can also include subtle morphological changes to the cell that is not well studied in the scientific literature. As such, by using the methods discussed above, the multi-perturbation interaction system 100 discovers (in an efficient manner) perturbation pairs with high potential for biologically meaningful interactions that may not be studied in the existing scientific literature.

In addition to the above description for synthetic lethality and morphological changes to the cell, in one or more embodiments, the multi-perturbation interaction system 100 further assists in analyzing various biological pathways. For instance, the multi-perturbation interaction system 100 analyzes amino acid sensing (e.g., mTOR pathway, which allows cells to dynamically respond to changes in nutrient availability and maintain cellular homeostasis), apoptosis (e.g., cell death), autophagy (e.g., the degradation and recycling of cellular components), ERAD (e.g., protein folding, which involves identifying and eliminating misfolded or improperly folded proteins), integrated stress response (e.g., a protective mechanism to restore cellular homeostasis and promote cell survival under adverse conditions), microtubule (e.g., which provide structural support to the cell to help maintain its shape), PI3K-Akt signaling (e.g., phosphatidylinositol 3-kinase (PI3K)-protein kinase B (Akt) pathway is a critical intracellular signaling pathway involved in regulating cell processes such as cell growth, survival, proliferation, metabolism, and motility), proteasome (e.g., a multi-subunit protein complex that degrades unwanted or damaged proteins), protein translation, protein translation (e.g., for the mTOR pathway which involves various cues such as nutrient availability, energy status, growth factors, and stress signals to regulate protein synthesis and cellular processes), ribosome (e.g., which are responsible for the synthesis of proteins through translation), transcriptional regulation (e.g., a process where information encoded in DNA is coped into RNA), UPR (e.g., unfolded protein response for protein folding which involves activating a pathway to respond to the accumulation of unfolded or misfolded proteins in the endoplasmic reticulum), mTOR signaling (e.g., a signaling pathway mediated by rapamycin), and p53 signaling (e.g., a cellular signaling pathway mediated by the tumor protein p53).

Moreover, although the above discussion heavily involves gene-gene interactions, in one or more embodiments, the multi-perturbation interaction system 100 further utilizes the principles above for gene-drug interactions (or drug-drug interactions). Specifically, for a given gene knockout, the multi-perturbation interaction system 100 can compare the gene knockout to a library of available drugs. For instance, the multi-perturbation interaction system 100 (e.g., rather than running all pairs of genes and drugs) can generate measures of biological interaction for existing gene-drug interactions and further generate a matrix that includes the existing data. Moreover, the multi-perturbation interaction system 100 can utilize the active-matrix completion techniques discussed above to select an entry of the matrix that corresponds to a high potential gene-drug pair for further experimentation.

As alluded to above, the multi-perturbation interaction system 100 extends to exploration spaces that can contain nonlinear interactions. In other words, the multi-perturbation interaction system 100 can identify a variety of high potential pairs in a variety of different problems and more efficiently search the state space to surface predictions for further testing.

Figure 9:
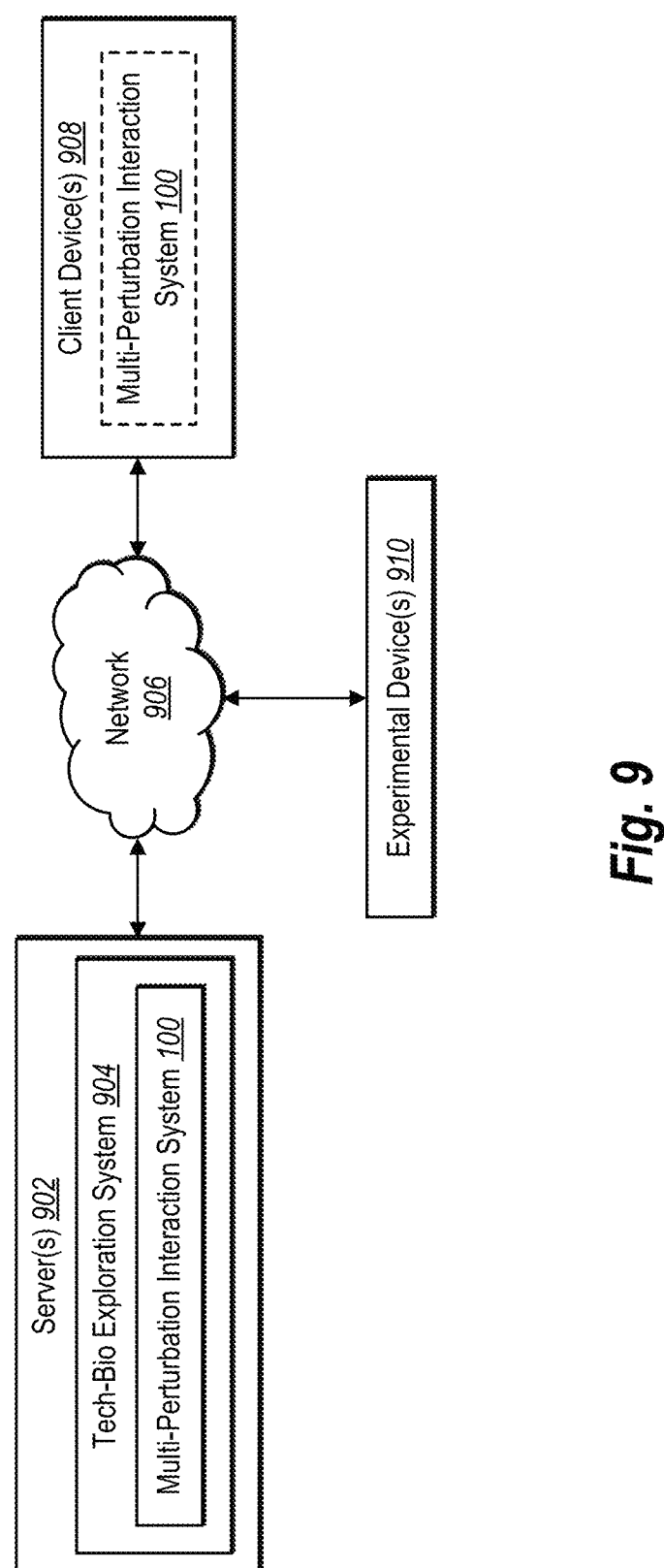
FIG. 9 illustrates an example environment of the multi-perturbation interaction system in accordance with one or more embodiments.

Additional detail regarding the multi-perturbation interaction system 100 environment will now be provided with reference to FIG. 9. In particular, FIG. 9 illustrates a schematic diagram of a system environment 900 in which the multi-perturbation interaction system 100 can operate in accordance with one or more embodiments.

As shown in FIG. 9, the environment includes server(s) 902 (which includes a tech-bio exploration system 904 and the multi-perturbation interaction system 100), a network 906, and client device(s) 908. As further illustrated in FIG. 9, the various computing devices within the environment can communicate via the network 906. Although FIG. 9 illustrates the multi-perturbation interaction system 100 being implemented by a particular component and/or device within the environment, the multi-perturbation interaction system 100 can be implemented, in whole or in part, by other computing devices and/or components in the environment (e.g., the additional device(s)). Additional description regarding the illustrated computing devices is provided with respect to FIG. 10 below.

As shown in FIG. 9, the server(s) 902 (e.g., one or more local servers operated by a particular entity) can include the tech-bio exploration system 904. In some embodiments, the tech-bio exploration system 904 can determine, store, generate, and/or display tech-bio information including maps of biology, experiments from various sources, and/or machine learning tech-bio predictions. For instance, the tech-bio exploration system 904 can analyze data signals corresponding to various treatments or interventions (e.g., compounds or biologics) and the corresponding relationships in genetics, proteomics, phenomics (i.e., cellular phenotypes), and invivomics (e.g., expressions or results within a living animal). Moreover, the tech-bio exploration system 904 provides an environment for operating, executing, and managing complex drug discovery pipelines.

For instance, the tech-bio exploration system 904 can generate and access experimental results corresponding to gene sequences, protein shapes/folding, protein/compound interactions, phenotypes resulting from various interventions or perturbations (e.g., gene knockout sequences or compound treatments), and/or in vivo experimentation on various treatments in living animals. By analyzing these signals (e.g., utilizing various machine learning models), the tech-bio exploration system 904 can generate or determine a variety of predictions and inter-relationships for improving treatments/interventions.

To illustrate, the tech-bio exploration system 904 can generate maps of biology indicating biological inter-relationships or similarities between these various input signals to discover potential new treatments as part of the complex compound discovery process. For example, the tech-bio exploration system 904 can utilize machine learning and/or maps of biology to identify a similarity between a first gene associated with disease treatment and a second gene previously unassociated with the disease based on a similarity in resulting phenotypes from gene knockout experiments. The tech-bio exploration system 904 can then identify new treatments based on the gene similarity (e.g., by targeting compounds the impact the second gene). Similarly, the tech-bio exploration system 904 can analyze signals from a variety of sources (e.g., protein interactions, or in vivo experiments) to predict efficacious treatments based on various levels of biological data.

The tech-bio exploration system 904 can generate GUIs comprising dynamic user interface elements to convey tech-bio information and receive user input for intelligently exploring tech-bio information. Indeed, as mentioned above, the tech-bio exploration system 904 can generate GUIs displaying different maps of biology that intuitively and efficiently express complex interactions between different biological systems for identifying improved treatment solutions. Furthermore, the tech-bio exploration system 904 can also electronically communicate tech-bio information between various computing devices.

As shown in FIG. 9, the tech-bio exploration system 904 can include a system that facilitates various models or algorithms for generating maps of biology (e.g., maps or visualizations illustrating similarities or relationships between genes, proteins, diseases, compounds, and/or treatments) and discovering new treatment options over one or more networks. For example, the tech-bio exploration system 904 collects, manages, and transmits data across a variety of different entities, accounts, and devices. In some cases, the tech-bio exploration system 904 is a network system that facilitates access to (and analysis of) tech-bio information within a centralized operating system. Indeed, the tech-bio exploration system 904 can link data from different network-based research institutions to generate and analyze maps of biology.

As shown in FIG. 9, the tech-bio exploration system 904 can include a system that comprises the multi-perturbation interaction system 100 that generates measures of biological interaction between perturbation pairs (e.g., gene pair knockouts) and further selects one or more additional perturbation pairs (e.g., based on a balance between reward and exploration) to initiate additional downstream exploration. For example, in context of the above description for the tech-bio exploration system 904, in some embodiments the tech-bio exploration system 904 further utilizes the multi-perturbation interaction system 100 to enhance the coordination between various groups involved in the drug discovery process. For instance, the multi-perturbation interaction system 100 works in tandem with the tech-bio exploration system 904 to identify perturbation pairs with a high potential with meaningful biological relationships (e.g., relationships between genes, proteins, diseases, compounds, and/or treatments). Further, the multi-perturbation interaction system 100 can utilize the identified perturbation pairs with high potential to initiate additional experimentation to efficiently explore a perturbation pair space for developing biological compounds (e.g., to target one or more perturbation pairs). Specifically, the tech-bio exploration system 904 utilizes the multi-perturbation interaction system 100 to generate measures of biological interaction, map the measures of biological interaction to a matrix and further utilize an active-matrix completion algorithm to make one or more selections for exploring a perturbation pair. Additionally, in some embodiments, the multi-perturbation interaction system 100 generates additional measures of biological interaction based on the additional exploration, updates the matrix, and further selects another entry from the matrix.

To further illustrate, the tech-bio exploration system 904 utilizes the multi-perturbation interaction system 100 at the program discovery phase to identify compounds that target certain genes. For instance, the multi-perturbation interaction system 100 can test various hypotheses for how a double perturbation (e.g., a double gene knockout) affects a cell (e.g., via synthetic lethality or morphological changes) and further utilizes the multi-perturbation interaction system 100 to efficiently explore the state space without performing brute-force searches.

As also illustrated in FIG. 9, the environment includes the client device(s) 908. As mentioned above, the client device(s) 908 can be involved in the process of drug discovery. Thus, for example, the client device(s) 908 can coordinate/manage generating measures of biological interaction, feeding the measures to an additional client device and further initiating the selection of an additional perturbation pair for downstream experimentation. For instance, the client device(s) 908 can coordinate/manage testing perturbation pairs under various conditions to further determine whether to initiate one or more programs (industrial program generation or industrial compound generation) for one or more of the perturbation pairs (e.g., developing drug compounds that target the perturbation pair).

To illustrate, the client device(s) 908 can include computing devices that implement or manage a compound program generation stage of a compound discovery process. Similarly, the client device(s) 908 can include computing devices that implement or manage a compound lead generation stage and the client device(s) 908 can include computing devices that implement or manage a compound/ dose selection stage. For example, the multi-perturbation interaction system 100 can receive one or more requests to make one or more selections of perturbation pairs based on the existing data related to measures of biological interactions.

In some embodiments, the environment also includes additional device(s). For example, the multi-perturbation interaction system 100 can utilize the additional device(s) to further operate and manage downstream operations after generating measures of biological interaction and selecting an additional perturbation pair. For instance, the additional device(s) include the experimental device(s) 910 (e.g., to expose a cell to the additional perturbation pair) and ana- lytical device(s) (e.g., to analyze the exposed cell, generate an image of the exposed cell, etc.). Further, in some instances, the additional device(s) also include the comput- ing devices discussed below in FIG. 11.

Furthermore, in one or more implementations, the client device(s) 908 include a client application. The client appli- cation can include instructions that (upon execution) cause the client device(s) 908 to perform various actions. For example, a user of a user account can interact with the client application on the client device(s) 908 to execute the gen- eration of a matrix that includes a plurality of measures of biological interactions and to begin an active-matrix completion task. For instance, in some embodiments the multi-perturbation interaction system 100 receives a request to generate a measure of biological interaction from experi- mental data that includes individual embeddings and a pairwise embedding. In response, the multi-perturbation interaction system 100 can generate the measure of biologi- cal interaction and provide an option for the client device(s) 908 to identify high potential perturbation pairs based on the existing data. In some instances, the multi-perturbation interaction system 100 selects a perturbation pair and in response, further causes the client device(s) 908 to further present options for executing an action (e.g., performing downstream experiments, tests, or evaluations for the selected perturbation pair).

Although not shown, the environment can also include dedicated training device(s). For example, the dedicated training device(s) can include computing devices or virtual machines dedicated to training or implementing a generative stochastic model (e.g., for exploring a state space), a machine learning model (e.g., for generating embeddings), a pairwise prediction model, and an active-matrix completion algorithm. For example, the dedicated training device(s) can provide datasets, parameters, objectives, and other learning constraints to train and/or implement the aforementioned models. Thus, the multi-perturbation interaction system 100 interacts with the dedicated training device(s) to learn cer- tain state spaces and to accurately generate corresponding outputs.

The environment can also include experimental device(s) 910. For example, the tech-bio exploration system 904 can interact with the experimental device(s) 910 that include intelligent robotic devices and camera devices for generating and capturing digital images of cellular phenotypes resulting from different perturbations (e.g., genetic knockouts or compound treatments of stem cells). Similarly, the experi- mental device(s) 910 can include camera devices and/or other sensors (e.g., heat or motion sensors) capturing real- time information from animals as part of in vivo experi- mentation. The tech-bio exploration system 904 can also interact with a variety of other experimental device(s) 910 such as devices for determining, generating, or extracting gene sequences or protein information. For example, the experimental device(s) 910 may include computing devices linked to biosensorselectrophysiological platforms, x-ray crystallography machines, liquid chromatography mass spectrometry systems, nuclear magnetic resonance spec- trometers, mass spectrometers. In some implementations, the multi-perturbation interaction system 100 selects a per- turbation pair and further determines to employ or utilize one or more experimental devices (e.g., to initiate one or more experiments based on the selection).

As further shown in FIG. 9, the environment includes the network 906. As mentioned above, the network 906 can enable communication between components of the environ- ment. In one or more embodiments, the network 906 may include a suitable network and may communicate using a various number of communication platforms and technolo- gies suitable for transmitting data and/or communication signals, examples of which are described with reference to FIG. 11. Furthermore, although FIG. 9 illustrates computing devices communicating via the network 906, the various components of the environment can communicate and/or interact via other methods (e.g., communicate directly).

FIGS. 1-10, the corresponding text, and the examples provide a number of different systems, methods, and non- transitory computer readable media for generating a measure of biological interaction from comparing individual pertur- bation embeddings and a pairwise embedding. In addition to the foregoing, embodiments can also be described in terms of flowcharts comprising acts for accomplishing a particular result. For example, FIG. 10 illustrates a flowchart of an example sequence of acts in accordance with one or more embodiments.

While FIG. 10 illustrates acts according to some embodi- ments, alternative embodiments may omit, add to, reorder, and/or modify any of the acts shown in FIG. 10. The acts of FIG. 10 can be performed as part of a method (e.g., a computer-implemented method). Alternatively, a non-tran- sitory computer readable medium can comprise instructions, that when executed by one or more processors (e.g., at least one processor), cause a computing device to perform the acts of FIG. 10. In still further embodiments, a system can perform the acts of FIG. 10. Additionally, the acts described herein may be repeated or performed in parallel with one another or in parallel with different instances of the same or other similar acts.

FIG. 10 illustrates an example series of acts 1000 for generating a measure of biological interaction in accordance with one or more embodiments. The series of acts 1000 can include an act 1002 of generating a first individual pertur- bation embedding and a second individual perturbation embedding, an act 1004 of determining a predicted pairwise embedding for the first perturbation and the second pertur- bation, an act 1006 of generating a pairwise embedding from an image portraying a cell exposed to the first perturbation and the second perturbation, and an act 1008 of generating a measure of biological interaction of the first perturbation and the second perturbation. Specifically, the series of acts 1000 can include acts 1102-1108 of generating, utilizing a machine learning model, a first individual perturbation embedding, from a first image of a first cell exposed to a first perturbation, and a second individual perturbation embed- ding, from a second image of a second cell exposed to a second perturbation; determining a predicted pairwise embedding for the first perturbation and the second pertur- bation by combining the first individual perturbation embed- ding and the second individual perturbation embedding;

generating, utilizing the machine learning model, a pairwise embedding from an image portraying a cell exposed to the first perturbation and the second perturbation; and generating a measure of biological interaction of the first perturbation and the second perturbation by comparing the predicted pairwise embedding with the pairwise embedding.

For example, in one or more embodiments, the series of acts 1000 includes generating the first individual perturbation embedding from the first cell exposed to a first individual gene knockout of a first gene. In one or more implementations, the series of acts 1000 includes generating the second individual perturbation embedding comprises from the second cell exposed to a second individual gene knockout of a second gene.

In addition, in one or more implementations, the series of acts 1000 includes determining a first normalized feature vector from the first individual perturbation embedding and a control embedding and a second normalized feature vector from the second individual perturbation embedding and the control embedding; and combining the first normalized feature vector and the second normalized feature vector to determine the predicted pairwise embedding for the first perturbation and the second perturbation.

Further, in some implementations, the series of acts 1000 includes generating the pairwise embedding from the image portraying the cell exposed to a double gene knockout of a first gene and a second gene.

In one or more implementations, the series of acts 1000 includes generating a matrix comprising a plurality of pairwise perturbations and corresponding measures of biological interactions. Moreover, in one or more implementations, the series of acts 1000 includes generating, utilizing a pairwise prediction model, a plurality of predicted pairwise perturbation interaction scores for individual perturbations and corresponding information gain predictions based on the matrix comprising the plurality of pairwise perturbations and the corresponding measures of biological interactions.

In addition, in some implementations, the series of acts 1000 includes utilizing an active-matrix completion algorithm to select a first entry from a plurality of entries of the matrix based on the plurality of predicted pairwise perturbation interaction scores for the individual perturbations and the corresponding information gain predictions.

In one or more implementations, the series of acts 1000 includes transmitting a perturbation pair corresponding to the first entry from the matrix to initiate additional experimental processes for generating an additional measure of biological interaction for the perturbation pair. Moreover, in one or more implementations, the series of acts 1000 includes based on determining the additional measure of biological interaction for the perturbation pair, updating the matrix to include the additional measure of biological interaction for the perturbation pair.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., memory), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed by a processor, cause a general-purpose computer, special purpose computer, or special purpose processing device to perform a certain function or group of functions. In some embodiments, computer-executable instructions are executed by a general-purpose computer to turn the general-purpose computer into a special purpose computer implementing elements of the disclosure. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. As used herein, the term "cloud computing" refers to a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In addition, as used herein, the term "cloud-computing environment" refers to an environment in which cloud computing is employed.

Figure 11:
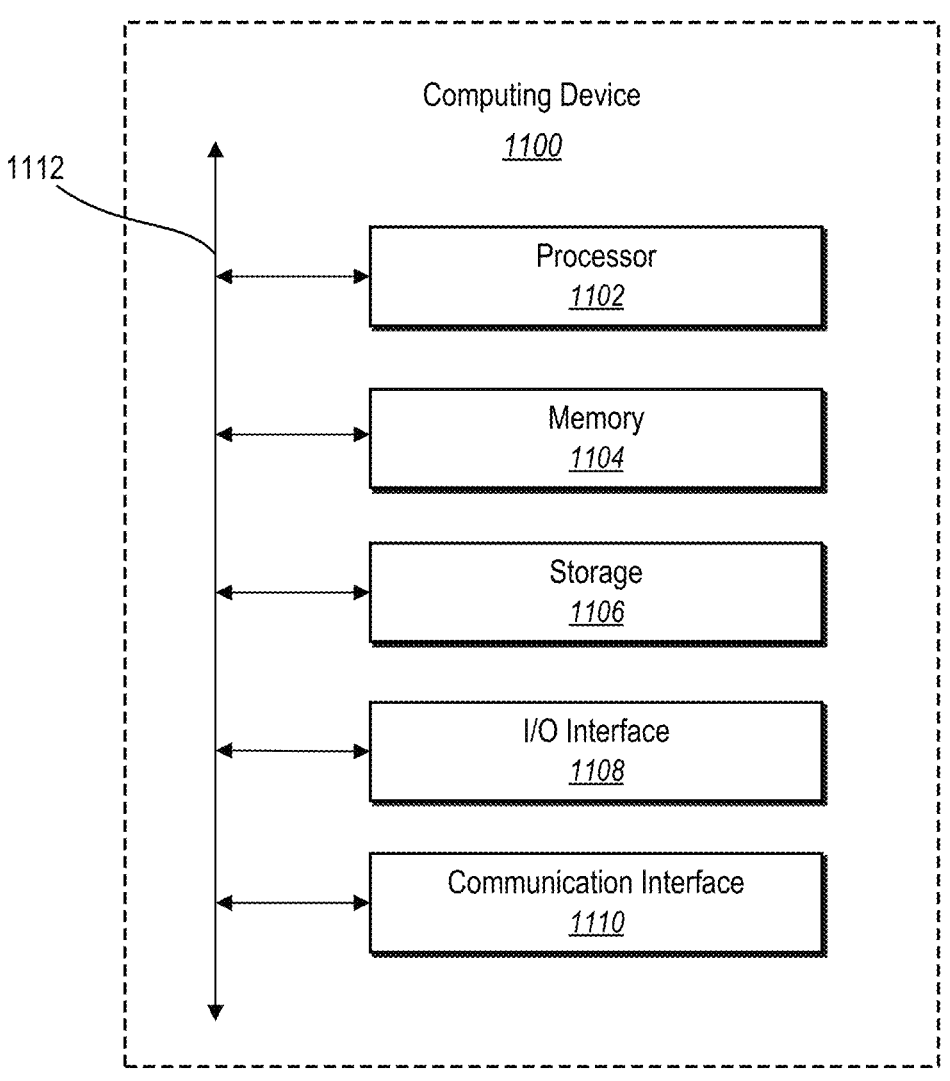
FIG. 11 illustrates a block diagram of a computing device for implementing one or more embodiments.

FIG. 11 illustrates a block diagram of an example computing device 1100 that may be configured to perform one or more of the processes described above. One will appreciate that one or more computing devices, such as the computing device 1100 may represent the computing devices described above. In one or more embodiments, the computing device 1100 may be a mobile device (e.g., a mobile telephone, a smartphone, a PDA, a tablet, a laptop, a camera, a tracker, a watch, a wearable device, etc.). In some embodiments, the computing device 1100 may be a non-mobile device (e.g., a desktop computer or another type of client device). Further, the computing device 1100 may be a server device that includes cloud-based processing and storage capabilities.

As shown in FIG. 11, the computing device 1100 can include one or more processor(s) 1102, memory 1104, a storage device 1106, input/output interfaces 1108 (or "I/O interfaces 1108"), and a communication interface 1110, which may be communicatively coupled by way of a communication infrastructure (e.g., bus 1112). While the computing device 1100 is shown in FIG. 11, the components illustrated in FIG. 11 are not intended to be limiting. Additional or alternative components may be used in other embodiments. Furthermore, in certain embodiments, the computing device 1100 includes fewer components than those shown in FIG. 11. Components of the computing device 1100 shown in FIG. 11 will now be described in additional detail.

In particular embodiments, the processor(s) 1102 includes hardware for executing instructions, such as those making up a computer program. As an example, and not by way of limitation, to execute instructions, the processor(s) 1102 may retrieve (or fetch) the instructions from an internal register, an internal cache, memory 1104, or a storage device 1106 and decode and execute them.

The computing device 1100 includes memory 1104, which is coupled to the processor(s) 1102. The memory 1104 may be used for storing data, metadata, and programs for execution by the processor(s). The memory 1104 may include one or more of volatile and non-volatile memories, such as Random-Access Memory ("RAM"), Read-Only Memory ("ROM"), a solid-state disk ("SSD"), Flash, Phase Change Memory ("PCM"), or other types of data storage. The memory 1104 may be internal or distributed memory.

The computing device 1100 includes a storage device 1106 includes storage for storing data or instructions. As an example, and not by way of limitation, the storage device 1106 can include a non-transitory storage medium described above. The storage device 1106 may include a hard disk drive (HDD), flash memory, a Universal Serial Bus (USB) drive or a combination these or other storage devices.

As shown, the computing device 1100 includes one or more I/O interfaces 1108, which are provided to allow a user to provide input to (such as user strokes), receive output from, and otherwise transfer data to and from the computing device 1100. These I/O interfaces 1108 may include a mouse, keypad or a keyboard, a touch screen, camera, optical scanner, network interface, modem, other known I/O devices or a combination of such I/O interfaces 1108. The touch screen may be activated with a stylus or a finger.

The I/O interfaces 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O interfaces 1108 are configured to provide graphical data to a display for presentation to a user. The graphical data may be representative of one or more graphical user interfaces and/or any other graphical content as may serve a particular implementation.

The computing device 1100 can further include a communication interface 1110. The communication interface 1110 can include hardware, software, or both. The communication interface 1110 provides one or more interfaces for communication (such as, for example, packet-based communication) between the computing device and one or more other computing devices or one or more networks. As an example, and not by way of limitation, communication interface 1110 may include a network interface controller (NIC) or network adapter for communicating with an Ethernet or other wire-based network or a wireless NIC (WNIC) or wireless adapter for communicating with a wireless network, such as a WI-FI. The computing device 1100 can further include a bus 1112. The bus 1112 can include hardware, software, or both that connects components of computing device 1100 to each other.

In one or more implementations, various computing devices can communicate over a computer network. This disclosure contemplates any suitable network. As an example, and not by way of limitation, one or more portions of a network may include an ad hoc network, an intranet, an extranet, a virtual private network ("VPN"), a local area network ("LAN"), a wireless LAN ("WLAN"), a wide area network ("WAN"), a wireless WAN ("WWAN"), a metropolitan area network ("MAN"), a portion of the Internet, a portion of the Public Switched Telephone Network ("PSTN"), a cellular telephone network, or a combination of two or more of these.

In particular embodiments, the computing device 1100 can include a client device that includes a requester application or a web browser, such as MICROSOFT INTERNET EXPLORER, GOOGLE CHROME, or MOZILLA FIREFOX, and may have one or more add-ons, plug-ins, or other extensions, such as TOOLBAR or YAHOO TOOLBAR. A user at the client device may enter a Uniform Resource Locator ("URL") or other address directing the web browser to a particular server (such as server), and the web browser may generate a Hyper Text Transfer Protocol ("HTTP") request and communicate the HTTP request to server. The server may accept the HTTP request and communicate to the client device one or more Hyper Text Markup Language ("HTML") files responsive to the HTTP request. The client device may render a webpage based on the HTML files from the server for presentation to the user. This disclosure contemplates any suitable webpage files. As an example, and not by way of limitation, webpages may render from HTML files, Extensible Hyper Text Markup Language ("XHTML") files, or Extensible Markup Language ("XML") files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, the tech-bio exploration system 904 may include a variety of servers, sub-systems, programs, modules, logs, and data stores. In particular embodiments, the tech-bio exploration system 904 may include one or more of the following: a web server, action logger, API-request server, transaction engine, cross-institution network interface manager, notification controller, action log, third-party-content-object-exposure log, inference module, authorization/privacy server, search module, user-interface module, user-profile (e.g., provider profile or requester profile) store, connection store, third-party content store, or location store. The tech-bio exploration system 904 may also include suitable components such as network interfaces, security mechanisms, load balancers, failover servers, management-and-network-operations consoles, other suitable components, or any suitable combination thereof. In particular embodiments, the tech-bio exploration system 904 may include one or more user-profile stores for storing user profiles and/or account information for credit accounts, secured accounts, secondary accounts, and other affiliated financial networking system accounts. A user profile may include, for example, biographic information, demographic information, financial information, behavioral information, social information, or other types of descriptive information, such as interests, affinities, or location.

The web server may include a mail server or other messaging functionality for receiving and routing messages between the tech-bio exploration system 904 and one or more client devices. An action logger may be used to receive communications from a web server about a user's actions on or off the tech-bio exploration system 904. In conjunction with the action log, a third-party-content-object log may be maintained of user exposures to third-party-content objects. A notification controller may provide information regarding content objects to a client device. Information may be pushed to a client device as notifications, or information may be pulled from a client device responsive to a request received from the client device. Authorization servers may be used to enforce one or more privacy settings of the users of the tech-bio exploration system 904. A privacy setting of a user determines how particular information associated with a user can be shared. The authorization server may allow users to opt in to or opt out of having their actions logged by the tech-bio exploration system 904 or shared with other systems, such as, for example, by setting appropriate privacy settings. Third-party-content-object stores may be used to store content objects received from third parties. Location stores may be used for storing location information received from a client device associated with users.

In the foregoing specification, the invention has been described with reference to specific example embodiments thereof. Various embodiments and aspects of the invention(s) are described with reference to details discussed herein, and the accompanying drawings illustrate the various embodiments. The description above and drawings are illustrative of the invention and are not to be construed as limiting the invention. Numerous specific details are described to provide a thorough understanding of various embodiments of the present invention.

The present invention may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel to one another or in parallel to different instances of the same or similar steps/acts. The scope of the invention is, therefore, indicated by the appended claims rather than by the foregoing description. All changes that come within the meaning and range of equivalency of the claims are to be embraced within their scope.

What is claimed is:

1. A method comprising:

receiving a first digital image of a first biological cell exposed to a first perturbation, wherein the first perturbation comprises a first gene knockout of a first gene of the first biological cell or a first compound treatment of the first biological cell;

generating, utilizing a neural network machine learning model, a first individual perturbation feature vector, from the first digital image of the first biological cell exposed to the first perturbation;

receiving a second digital image of a second biological cell exposed to a second perturbation, wherein the second perturbation comprises a second gene knockout of a second gene of the second biological cell or a second compound treatment of the second biological cell;

generating, utilizing the neural network machine learning model, a second individual perturbation feature vector, from the second digital image of the second biological cell exposed to the second perturbation;

generating a predicted pairwise feature vector for the first biological cell individually exposed to the first perturbation and the second biological cell individually exposed to the second perturbation by combining the first individual perturbation feature vector and the
second individual perturbation feature vector;

receiving a third digital image of a third biological cell
exposed to a perturbation pair comprising both the first
perturbation and the second perturbation;

generating, utilizing the neural network machine learning
model, a double perturbation pairwise feature vector
from the third digital image of the third biological cell
exposed to the perturbation pair comprising both the
first perturbation and the second perturbation;

generating a measure of biological interaction between
the first perturbation and the second perturbation by
comparing the predicted pairwise feature vector from
the first digital image and the second digital image with
the double perturbation pairwise feature vector from
the third digital image, wherein the measure of bio-
logical interaction indicates a difference between bio-
logical cell response from exposure to the first pertur-
bation and the second perturbation individually relative
to biological cell response from exposure to the first
perturbation and the second perturbation in combina-
tion;

generating an incomplete biological interaction matrix
arranged according to a plurality of perturbation pairs,
wherein the incomplete biological interaction matrix
comprises the measure of biological interaction for the
perturbation pair as an entry in the incomplete biologi-
cal interaction matrix and further comprises additional
measures of biological interactions as additional entries
in the incomplete biological interaction matrix that
correspond to additional perturbation pairs of the plu-
rality of perturbation pairs;

generating, utilizing an active learning model that takes as
inputs entries comprising the measure of biological
interaction and the additional measures of biological
interaction in the incomplete biological interaction
matrix, predicted pairwise perturbation interaction
scores corresponding to incomplete entries in the
incomplete biological interaction matrix;

based on the predicted pairwise perturbation interaction
scores, selecting additional perturbations for experi-
mentation from the incomplete biological interaction
matrix, wherein the additional perturbations for experi-
mentation correspond to incomplete entries in the
incomplete biological interaction matrix; and performing a downstream experiment for a fourth bio-
logical cell by perturbing the fourth biological cell
according to the additional perturbations selected from
the incomplete biological interaction matrix.

2. The method of claim 1, wherein:

receiving the first digital image comprises receiving a first
captured image of the first biological cell with a first
modified cell phenotype resulting from the first gene
knockout of the first gene; and receiving the second digital image comprises receiving a
second captured image of the second biological cell
with a second modified cell phenotype resulting from
the second gene knockout of the second gene.

3. The method of claim 1, wherein determining the
predicted pairwise feature vector for the first perturbation
and the second perturbation comprises:

determining a first normalized feature vector from the first
individual perturbation feature vector and a control
feature vector and a second normalized feature vector
from the second individual perturbation feature vector
and the control feature vector; and combining the first normalized feature vector and the
second normalized feature vector to determine the
predicted pairwise feature vector for the first perturba-
tion and the second perturbation.

4. The method of claim 1, further comprising generating
the double perturbation pairwise feature vector from the
third digital image portraying the third biological cell
exposed to a double gene knockout of the first gene and the
second gene in the third biological cell.

5. The method of claim 1, wherein generating the incom-
plete biological interaction matrix comprises generating a
matrix that includes pairwise perturbation experiment data
corresponding to actual pairwise perturbations and predic-
tions of measures of biological interactions corresponding to
perturbation pairs.

6. The method of claim 5, further comprises generating,
utilizing the active learning model that comprises a pairwise
prediction model, the predicted pairwise perturbation inter-
action scores for individual perturbations and corresponding
information gain predictions based on the incomplete bio-
logical interaction matrix, wherein the corresponding infor-
mation gain predictions indicate an amount of potential
increase in knowledge relative to the incomplete biological
interaction matrix in response to a selection of the additional
perturbations for experimentation.

7. The method of claim 6, wherein utilizing the active
learning model comprises an active-matrix completion algo-
rithm to select a first entry from a plurality of entries of the
incomplete biological interaction matrix based on the pre-
dicted pairwise perturbation interaction scores for the indi-
vidual perturbations and the corresponding information gain
predictions.

8. The method of claim 1, further comprising:

based on performing the downstream experiment for the
fourth biological cell, determining additional measure
of biological interaction for the additional perturbations
selected from the incomplete biological interaction
matrix; and updating the incomplete biological interaction matrix to
include the additional measure of biological interaction
for the additional perturbations.

9. A method comprising:

receiving a first digital image of a first biological cell
exposed to a first gene knockout of a first gene of the
first biological cell;

generating, utilizing a neural network machine learning
model, a first individual perturbation feature vector,
from the first digital image of the first biological cell
exposed to the first gene knockout;

receiving a second digital image of a second biological
cell exposed to a second gene knockout of a second
gene of the second biological cell;

generating, utilizing the neural network machine learning
model, a second individual perturbation feature vector,
from the second digital image of the second biological
cell exposed to the second gene knockout;

generating a predicted pairwise feature vector for the first
biological cell individually exposed to the first gene
knockout and the second biological cell individually
exposed to the second gene knockout by combining the
first individual perturbation feature vector and the
second individual perturbation feature vector;

receiving a third digital image of a third biological cell
exposed to a gene knockout pair comprising both the
first gene knockout and the second gene knockout;

generating, utilizing the neural network machine learning
model, a double perturbation pairwise feature vector from the third digital image of the third biological cell exposed to the gene knockout pair comprising both the first gene knockout and the second gene knockout;

generating a measure of biological interaction between the first gene knockout and the second gene knockout by comparing the predicted pairwise feature vector from the first digital image and the second digital image with the double perturbation pairwise feature vector from the third digital image, wherein the measure of biological interaction indicates a difference between biological cell response from exposure to the first gene knockout and the second gene knockout individually relative to biological cell response from exposure to the first gene knockout and the second gene knockout in combination;

generating an incomplete biological interaction matrix arranged according to a plurality of gene knockout pairs, wherein the incomplete biological interaction matrix comprises the measure of biological interaction for the gene knockout pair as an entry in the incomplete biological interaction matrix and further comprises additional measures of biological interactions as additional entries in the incomplete biological interaction matrix that correspond to additional gene knockout pairs of the plurality of gene knockout pairs;

generating, utilizing an active learning model that takes as inputs entries comprising the measure of biological interaction and the additional measures of biological interaction in the incomplete biological interaction matrix, predicted pairwise perturbation interaction scores corresponding to incomplete entries in the incomplete biological interaction matrix;

based on the predicted pairwise perturbation interaction scores, selecting additional gene knockouts for experimentation from the incomplete biological interaction matrix, wherein the additional gene knockouts for experimentation correspond to incomplete entries in the incomplete biological interaction matrix; and performing a downstream experiment for a fourth biological cell by applying the additional gene knockouts selected from the incomplete biological interaction matrix to the fourth biological cell.

10. The method of claim 9, wherein:

receiving the first digital image comprises receiving a first captured image of the first biological cell with a first modified cell phenotype resulting from the first gene knockout of the first gene; and receiving the second digital image comprises receiving a second captured image of the second biological cell with a second modified cell phenotype resulting from the second gene knockout of the second gene.

11. The method of claim 9, wherein determining the predicted pairwise feature vector for the first gene knockout and the second gene knockout comprises:

determining a first normalized feature vector from the first individual perturbation feature vector and a control feature vector and a second normalized feature vector from the second individual perturbation feature vector and the control feature vector; and combining the first normalized feature vector and the second normalized feature vector to determine the predicted pairwise feature vector for the first gene knockout and the second gene knockout.

12. The method of claim 9, further comprising generating the double perturbation pairwise feature vector from the third digital image portraying the third biological cell exposed to a double gene knockout of the first gene and the second gene in the third biological cell.

13. The method of claim 9, wherein generating the incomplete biological interaction matrix comprises generating a matrix that includes pairwise perturbation experiment data corresponding to actual pairwise perturbations and predictions of measures of biological interactions corresponding to perturbation pairs.

14. The method of claim 9, further comprising generating, utilizing the active learning model that comprises a pairwise prediction model, the predicted pairwise perturbation interaction scores for individual gene knockouts and corresponding information gain predictions based on the incomplete biological interaction matrix, wherein the corresponding information gain predictions indicate an amount of potential increase in knowledge relative to the incomplete biological interaction matrix in response to a selection of the additional gene knockouts for experimentation.

15. The method of claim 14, wherein utilizing the active learning model comprises utilizing an active-matrix completion algorithm to select a first entry from a plurality of entry pairs of the incomplete biological interaction matrix based on the predicted pairwise perturbation interaction scores for the individual gene knockouts and the corresponding information gain predictions.

16. A method comprising:

capturing, utilizing one or more digital cameras, a first digital image of a first biological cell exposed to a first perturbation, wherein the first perturbation comprises a first gene knockout of a first gene of the first biological cell or a first compound treatment of the first biological cell;

generating, utilizing a neural network machine learning model, a first individual perturbation feature vector, from the first digital image of the first biological cell exposed to the first perturbation;

capturing, utilizing the one or more digital cameras, a second digital image of a second biological cell exposed to a second perturbation, wherein the second perturbation comprises a second gene knockout of a second gene of the second biological cell or a second compound treatment of the second biological cell;

generating, utilizing the neural network machine learning model, a second individual perturbation feature vector, from the second digital image of the second biological cell exposed to the second perturbation;

generating a predicted pairwise feature vector for the first biological cell individually exposed to the first perturbation and the second biological cell individually exposed to the second perturbation by combining within a machine learning feature space, the first individual perturbation feature vector and the second individual perturbation feature vector;

capturing, utilizing the one or more digital cameras, a third digital image of a third biological cell exposed to a perturbation pair comprising both the first perturbation and the second perturbation;

generating, utilizing the neural network machine learning model, a double perturbation pairwise feature vector from the third digital image of the third biological cell exposed to the perturbation pair comprising both the first perturbation and the second perturbation;

generating a measure of biological interaction between the first perturbation and the second perturbation by comparing the predicted pairwise feature vector from the first digital image and the second digital image with the double perturbation pairwise feature vector from the third digital image, wherein the measure of biological interaction indicates a difference between biological cell response from exposure to the first perturbation and the second perturbation individually relative to biological cell response from exposure to the first perturbation and the second perturbation in combination;

generating an incomplete biological interaction matrix arranged according to a plurality of perturbation pairs, wherein the incomplete biological interaction matrix comprises the measure of biological interaction for the perturbation pair as an entry in the incomplete biological interaction matrix and further comprises additional measures of biological interactions as additional entries in the incomplete biological interaction matrix that correspond to additional perturbation pairs of the plurality of perturbation pairs;

generating, utilizing an active learning model that takes as inputs entries comprising the measure of biological interaction and the additional measures of biological interaction in the incomplete biological interaction matrix, predicted pairwise perturbation interaction scores corresponding to incomplete entries in the incomplete biological interaction matrix;

based on the predicted pairwise perturbation interaction scores, selecting additional perturbations for experimentation from the incomplete biological interaction matrix, wherein the additional perturbations for experimentation correspond to incomplete entries in the incomplete biological interaction matrix;

performing a downstream experiment for a fourth biological cell by perturbing, utilizing an experimental device, the fourth biological cell according to the additional perturbations selected from the incomplete biological interaction matrix; and capturing, utilizing the one or more digital cameras, a fourth digital image of the fourth biological cell exposed to the additional perturbations selected from the incomplete biological interaction matrix.

17. The method of claim 16, wherein:

receiving the first digital image comprises receiving a first captured image of the first biological cell with a first modified cell phenotype resulting from the first gene knockout of the first gene; and receiving the second digital image comprises receiving a second captured image of the second biological cell with a second modified cell phenotype resulting from the second gene knockout of the second gene.

18. The method of claim 16, wherein determining the predicted pairwise feature vector for the first perturbation and the second perturbation comprises:

determining a first normalized feature vector from the first individual perturbation feature vector and a control feature vector and a second normalized feature vector from the second individual perturbation feature vector and the control feature vector; and combining the first normalized feature vector and the second normalized feature vector to determine the predicted pairwise feature vector for the first perturbation and the second perturbation.

19. The method of claim 16, further comprising generating the double perturbation pairwise feature vector from the third digital image portraying the third biological cell exposed to a double gene knockout of the first gene and the second gene in the third biological cell.

20. The method of claim 16, wherein generating the incomplete biological interaction matrix comprises generating a matrix that includes pairwise perturbation experiment data corresponding to actual pairwise perturbations and predictions of measures of biological interactions corresponding to perturbation pairs.

* * * * *